United States Patent
daCosta et al.

(10) Patent No.: US 8,688,468 B1
(45) Date of Patent: Apr. 1, 2014

(54) SYSTEMS AND METHODS FOR VERIFYING DOSAGES ASSOCIATED WITH HEALTHCARE TRANSACTIONS

(75) Inventors: Patricia A. daCosta, Marietta, GA (US); Linda Henderson George, Temple, GA (US)

(73) Assignee: McKesson Financial Holdings, Hamilton (BM)

( * ) Notice: Subject to any disclaimer, the term of this patent is extended or adjusted under 35 U.S.C. 154(b) by 189 days.

(21) Appl. No.: 12/750,206

(22) Filed: Mar. 30, 2010

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2, 3
See application file for complete search history.

(56) References Cited

U.S. PATENT DOCUMENTS

| | | |
|---|---|---|
| 4,547,851 A | 10/1985 | Kurland |
| 5,048,870 A | 9/1991 | Mangini et al. |
| 5,235,702 A | 8/1993 | Miller |
| 5,301,105 A | 4/1994 | Cummings |
| 5,359,509 A | 10/1994 | Little et al. |
| 5,544,044 A | 8/1996 | Leatherman |
| 5,550,734 A | 8/1996 | Tarter et al. |
| 5,628,530 A | 5/1997 | Thornton |
| 5,644,778 A | 7/1997 | Burks et al. |
| 5,704,044 A | 12/1997 | Tarter et al. |
| 5,737,539 A | 4/1998 | Edelson et al. |
| 5,740,268 A | 4/1998 | Nishikawa et al. |
| 5,748,907 A | 5/1998 | Crane |
| 5,749,907 A | 5/1998 | Mann |
| 5,832,447 A | 11/1998 | Rieker et al. |
| 5,845,255 A | 12/1998 | Mayaud |
| 5,892,900 A | 4/1999 | Ginter et al. |
| 5,915,971 A | 6/1999 | Ramsay et al. |
| 5,950,169 A | 9/1999 | Borghesi et al. |
| 5,950,630 A | 9/1999 | Portwood et al. |
| 5,956,736 A | 9/1999 | Hanson et al. |
| 5,958,930 A | 9/1999 | Gangjee |
| 5,963,915 A | 10/1999 | Kirsch |

(Continued)

FOREIGN PATENT DOCUMENTS

CA 2482370 A1 3/2006
EP 1310895 A2 11/2002

(Continued)

OTHER PUBLICATIONS

ASHP Advantage, "Improving Medication Safety in Health Systems thorugh innovations in Automation Technology" ASHP Midyear Clinical Meeting Dec. 2004.*

(Continued)

*Primary Examiner* — Neal Sereboff
(74) *Attorney, Agent, or Firm* — Sutherland Asbill & Brennan LLP

(57) ABSTRACT

Systems and methods are provided for verifying dosages associated with healthcare transactions. A healthcare transaction may be received from a healthcare provider computer. The received healthcare transaction may include information associated with a patient and a prescribed product. Based at least in part on the received information, an age of the patient may be determined. Based upon the determined age, a probable weight for the patient may be determined. The probable weight may be utilized to determine whether a prescribed dosage for the product is an appropriate dosage for the patient.

18 Claims, 8 Drawing Sheets

(56) References Cited

U.S. PATENT DOCUMENTS

| | | | |
|---|---|---|---|
| 5,991,750 A | 11/1999 | Watson | |
| 6,006,242 A | 12/1999 | Poole et al. | |
| 6,012,035 A | 1/2000 | Freeman et al. | |
| 6,073,104 A | 6/2000 | Field | |
| 6,195,612 B1 | 2/2001 | Pack-Harris | |
| 6,202,923 B1 | 3/2001 | Boyer et al. | |
| 6,224,387 B1 | 5/2001 | Jones | |
| 6,272,472 B1 | 8/2001 | Danneels et al. | |
| 6,307,940 B1 | 10/2001 | Yamamoto et al. | |
| 6,324,516 B1 | 11/2001 | Shults et al. | |
| 6,330,546 B1 | 12/2001 | Gopinathan et al. | |
| 6,341,265 B1 | 1/2002 | Provost et al. | |
| 6,343,271 B1 | 1/2002 | Peterson et al. | |
| 6,427,020 B1 | 7/2002 | Rhoads | |
| 6,529,892 B1 | 3/2003 | Lambert | |
| 6,632,251 B1 | 10/2003 | Rutten et al. | |
| 6,671,692 B1 | 12/2003 | Marpe et al. | |
| 6,671,693 B1 | 12/2003 | Marpe et al. | |
| 6,694,334 B2 | 2/2004 | DuLong et al. | |
| 6,714,918 B2 | 3/2004 | Hillmer et al. | |
| 6,757,898 B1 | 6/2004 | Ilsen et al. | |
| 6,769,228 B1 | 8/2004 | Mahar | |
| 6,879,959 B1 | 4/2005 | Chapman et al. | |
| 6,978,286 B2 | 12/2005 | Francis et al. | |
| 7,013,284 B2 | 3/2006 | Guyan et al. | |
| 7,028,723 B1 | 4/2006 | Alouani et al. | |
| 7,111,173 B1 | 9/2006 | Scheidt | |
| 7,155,397 B2 | 12/2006 | Alexander et al. | |
| 7,356,460 B1 | 4/2008 | Kennedy et al. | |
| 7,380,707 B1 | 6/2008 | Fredman | |
| 7,401,027 B2 | 7/2008 | Moore et al. | |
| 7,418,400 B1 | 8/2008 | Lorenz | |
| 7,490,047 B2 | 2/2009 | Brown et al. | |
| 7,490,049 B2 | 2/2009 | Miller et al. | |
| 7,493,263 B2 | 2/2009 | Helmus et al. | |
| 7,519,540 B2 | 4/2009 | Mayaud | |
| 7,555,435 B2 | 6/2009 | Ball et al. | |
| 7,711,583 B2 | 5/2010 | Epstein et al. | |
| 7,716,068 B2 | 5/2010 | Ball et al. | |
| 7,720,694 B2 | 5/2010 | Potuluri et al. | |
| 7,801,642 B2 | 9/2010 | Ansari et al. | |
| 8,046,242 B1 | 10/2011 | daCosta et al. | |
| 2001/0001014 A1 | 5/2001 | Glendon, III et al. | |
| 2001/0032099 A1 | 10/2001 | Joao | |
| 2001/0037216 A1 | 11/2001 | Oscar et al. | |
| 2001/0037224 A1 | 11/2001 | Eldridge et al. | |
| 2001/0041993 A1 | 11/2001 | Campbell | |
| 2001/0056358 A1 | 12/2001 | Dulong et al. | |
| 2002/0002495 A1 | 1/2002 | Ullman | |
| 2002/0035488 A1 | 3/2002 | Aquila et al. | |
| 2002/0042725 A1 | 4/2002 | Mayaud | |
| 2002/0044043 A1 | 4/2002 | Chaco et al. | |
| 2002/0049617 A1 | 4/2002 | Lencki et al. | |
| 2002/0055856 A1 | 5/2002 | Adams | |
| 2002/0065687 A1 | 5/2002 | Onoue | |
| 2002/0087554 A1 | 7/2002 | Seelinger | |
| 2002/0087583 A1 | 7/2002 | Morgan et al. | |
| 2002/0111832 A1 | 8/2002 | Judge | |
| 2002/0120473 A1 | 8/2002 | Wiggins | |
| 2002/0128883 A1 | 9/2002 | Harris | |
| 2002/0133503 A1 | 9/2002 | Amar et al. | |
| 2002/0138593 A1 | 9/2002 | Novak et al. | |
| 2002/0175370 A1 | 11/2002 | Bockelman | |
| 2002/0183979 A1 | 12/2002 | Wildman | |
| 2002/0198831 A1 | 12/2002 | Patricelli et al. | |
| 2003/0009357 A1 | 1/2003 | Pish | |
| 2003/0009367 A1 | 1/2003 | Morrison | |
| 2003/0028404 A1 | 2/2003 | Herron et al. | |
| 2003/0050799 A1 | 3/2003 | Jay et al. | |
| 2003/0074222 A1 | 4/2003 | Rosow et al. | |
| 2003/0083903 A1 | 5/2003 | Myers | |
| 2003/0120588 A1 | 6/2003 | Dodd et al. | |
| 2003/0149594 A1 | 8/2003 | Beazley et al. | |
| 2003/0149625 A1 | 8/2003 | Leonardi et al. | |
| 2003/0154163 A1 | 8/2003 | Phillips et al. | |
| 2003/0158755 A1 | 8/2003 | Neuman | |
| 2003/0229540 A1 | 12/2003 | Algiene | |
| 2004/0006490 A1 | 1/2004 | Gingrich et al. | |
| 2004/0019464 A1 | 1/2004 | Martucci et al. | |
| 2004/0039599 A1 | 2/2004 | Fralic | |
| 2004/0046020 A1 | 3/2004 | Andreasson et al. | |
| 2004/0054685 A1 | 3/2004 | Rahn et al. | |
| 2004/0059600 A1 | 3/2004 | Ball | |
| 2004/0059601 A1 | 3/2004 | Ball | |
| 2004/0059602 A1 | 3/2004 | Ball | |
| 2004/0059607 A1 | 3/2004 | Ball | |
| 2004/0073457 A1 | 4/2004 | Kalies | |
| 2004/0078234 A1 | 4/2004 | Tallal, Jr. et al. | |
| 2004/0093242 A1 | 5/2004 | Cadigan et al. | |
| 2004/0111291 A1 | 6/2004 | Dust et al. | |
| 2004/0117323 A1 | 6/2004 | Mindala | |
| 2004/0148198 A1 | 7/2004 | Kalies | |
| 2004/0172281 A1 | 9/2004 | Stanners | |
| 2004/0188998 A1 | 9/2004 | Henthorn | |
| 2004/0249745 A1 | 12/2004 | Baaren | |
| 2005/0015280 A1 | 1/2005 | Gabel et al. | |
| 2005/0033604 A1 | 2/2005 | Hogan | |
| 2005/0048666 A1* | 3/2005 | Larson et al. | 436/169 |
| 2005/0060197 A1* | 3/2005 | Mayaud | 705/2 |
| 2005/0060201 A1 | 3/2005 | Connely, III et al. | |
| 2005/0065821 A1 | 3/2005 | Kalies | |
| 2005/0102169 A1 | 5/2005 | Wilson | |
| 2005/0125292 A1 | 6/2005 | Kassab et al. | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240473 A1 | 10/2005 | Ayers, Jr. et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0039966 A1 | 2/2006 | Miller et al. | |
| 2006/0085230 A1 | 4/2006 | Brill et al. | |
| 2006/0095300 A1* | 5/2006 | Schrier et al. | 705/3 |
| 2006/0136268 A1 | 6/2006 | Ash et al. | |
| 2006/0149784 A1 | 7/2006 | Tholl et al. | |
| 2006/0184391 A1 | 8/2006 | Barre et al. | |
| 2006/0247948 A1 | 11/2006 | Ellis et al. | |
| 2006/0259363 A1 | 11/2006 | Jhetam | |
| 2006/0271405 A1 | 11/2006 | Cipolle et al. | |
| 2007/0005402 A1 | 1/2007 | Kennedy et al. | |
| 2007/0050209 A1 | 3/2007 | Yered | |
| 2007/0083392 A1* | 4/2007 | Zaleski | 705/2 |
| 2007/0100662 A1 | 5/2007 | Suwalski et al. | |
| 2007/0136100 A1 | 6/2007 | Daugherty et al. | |
| 2007/0214009 A1 | 9/2007 | Epstein et al. | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2008/0262868 A1 | 10/2008 | Malolepszy | |
| 2008/0312957 A1 | 12/2008 | Luciano et al. | |
| 2009/0138281 A1* | 5/2009 | Hacker | 705/3 |
| 2009/0210252 A1 | 8/2009 | Silver | |
| 2009/0277516 A1 | 11/2009 | Winkler et al. | |
| 2010/0010909 A1 | 1/2010 | Marshall et al. | |
| 2011/0029321 A1 | 2/2011 | Rourke et al. | |

FOREIGN PATENT DOCUMENTS

| | | | |
|---|---|---|---|
| WO | WO 9106917 A1 | 5/1991 | |
| WO | WO 9503569 A3 | 2/1995 | |
| WO | WO 9725682 A1 | 7/1997 | |
| WO | WO 9850871 A1 | 11/1998 | |
| WO | WO 0039737 A1 | 7/2000 | |
| WO | WO 2007025295 A2 | 3/2007 | |

OTHER PUBLICATIONS

Charlie Croc."Greater than and less thanw ith Charlie Croc." CJS 2008.*

Metzger et al., "Computerized Physician Order Entry" Dec. 2001.*

McKesson, "Case Study—Memorial Health System" Oct. 2006.*

Potts et al. "Computerized Physician Order Entry and Medication Errors in a Pediatric Critical Care Unit" NeoReviews—Pediatrics 2004; 113;59.*

(56) References Cited

OTHER PUBLICATIONS

So et al., "Evaluation of the Accuracy of Different Methods Used to Estimate Weights in the Pediatric Population" Pediatrics 2009;123;e1045.*
McKesson Corporation, "Automate Medication Safety from the Dockside to the Bedside" vol. 2. Issue 3, 2008.*
CDC, "Birth to 36 months: Girls" May 2000.*
CDC, "Birth to 36 months: Boys" May 2000.*
Fomon et al., "Reference Data for Evaluating Infant Formulas Gains in Weight and Length of Term Infants" Nov. 2002.*
Rogoski, Richard "Putting patients first: regardless of the application implemented, healthcare organizations are on a steadfast mission to improve patient safety with the use of IT systems" Health Management Technology Feb. 2005.*
CDC, "2 to 20 years: Boys" May 2000.*
CDC, "2 to 20 years: Girls" May 2000.*
Nightingale et al., "Implementation of rules based computerised bedside prescribing and administration: itervention study" BMJ vol. 320, Mar. 18, 2000.*
Non-Final Office Action dated Dec. 15, 2010 in U.S. Appl. No. 12/357,882.
Non-Final Office Action for U.S. Appl. No. 12/571,152 mailed Dec. 5, 2011.
Non-Final Office Action for U.S. Appl. No. 12/748,129 mailed Jan. 24, 2012.
Sampson. R.J., Taking Control of Health Care Costs, Best's Review—Life Health Insurance Edition, Nov. 1983, pp. 64-66, vol. 84, Issue 7, USA.
Anonymous, ACS to Demonstrate Electronic Health Record Solution Suite at MMIS 2007 Conference, EHR Tools Consolidate Data, Provide Useful Information at the Point of Care for Medicaid Providers, Payers, and Patients, PR Newswire, Aug. 13, 2007, New York, NY, USA.
Lamb, J,, New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.
Anonymous, Pharmacy Industry Leaders Launch Firm to Supply Real-Time Data. PR Newswire. Jul. 30, 2001, p. 1. New York, NY, USA.
Anonymous, Medic; On-line Goes In-House, Chain Store Age Executive, Jan. 1987, pp. 128-132, vol. 63, Issue 1, USA.
Anonymous, TechRx Announces Successful Beta Deployment of T-Rex. PR Newwire. May 13, 2002.
"Two automatic identification technology, neither new in the sense if being recent developments . . . " Patient Safety & Quality Healthcare [Online] Aug. 2005. URL: http://www.awarix.com.
"Subnotebooks, Phones, and More. St. Vincent's Gets on Track." Mobile Health Data [Online], Nov. 19, 2004. URL: http://www.awarix.com.
"Coping with Information Overload." The News Source for Healthcare Information Technology [Online] Nov. 2004. URL: http://www.awarix.com.
"St. Vincent's first to use Birmingham startup's information system." The Birmingham News [Online] Apr. 11, 2005. URL: http://www.awarix.com.
"St. Vincent's is Digital Flagship" D. Lockridge; Birmingham Medical News [Online] Sep. 2005.
PR Newswire, "NDCHealth Annouces NDC Rx Safety Advisor to Help Prevent Look-Alike Sound-Alike Dispensation Errors", New York: Aug. 12, 2002.p. 1.
FDA Alert, Aug. 8, 2008 Drugs, Information for Healthcare Professionals—Simvastatin (marketed as Zocor and generics). Ezetimibe/Simvastatin (marketed as Vytorin), Niacin extended-release/Simvastatin (marketed as Simcor), used with Amiodarone (Cordarone. Pacerone), obtained from fda.gov/Drugs/DrugSafety Website on Sep. 15, 2009.
Drug Sheet entitled: Generic Name: Iovastatin, Brand Name: Mevacor, Altoprev.

Anonymous, Recommendations for the Use of 3-Hydroxy-3-methylglutaryl Coenzyme A Reductase Inhibitors (statins) i Veteran Patients Receiving Medications with the Potential for Drug-Drug Interactions. Nov. 2001.
Jerilyn B. Petropoulos and Christina E. Bello-Quintero, Frequency of Simvastatin Prescriptions with Potentially Interacting Mediations in a Veterans Affitirs Health Care System, Journal of Managed Care Pharmacy, pp. 239-242, vol. 10, No. 3, May/Jun. 2004.
Joseph M. Khahwaji and Ryszard R. Dudek, How Can We Manage Hyperlipidemia and Avoid Rhabdomyolysis in Transplant Patients?, The Permanente Journal/Fall 2006/vol. 10, No. 3.
Drug-Drug, Drug-Dietary Supplement, and Other Interactions, Regulatory Science.
Helen Fields, Doctors Often Ignore 'Black Box' Warnings on Prescription Drugs, Nov. 18, 2005.
How Often do Doctors Ignore Drug Interaction Warnings Generated by Electronic Prescribing Systems? Feb. 23, 2009, KevinMD.com~medical weblog.
Martin Kohl, Although There Aren't Any Perfect Solutions to Creating a Formulary Free of Drug-drug Interactions, There are Things You Can Do to Limit Problems.
Office Action dated Apr. 19, 2007, in U S. Appl. No. 10/339,230.
Final Office Action dated Oct. 18, 2007 in U.S. Appl. No. 10/339,230.
Office Action dated Feb. 28, 2008 in U.S. Appl. No. 10/339,230.
Final Office Action dated Sep. 29, 2008 in U.S. Appl. No. 10/339,230.
Non-Final Office Action dated Mar. 27, 2009 in U.S. Appl. No. 10/339,230.
Notice of Allowance for U.S. Appl. No. 10/339,230, date mailed by USPTO, Apr. 9, 2009.
Final Office Action dated Sep. 11, 2009 in U.S. Appl. No. 10/339,230.
Office Action dated Aug. 22, 2007 in U.S. Appl. No. 10/339,000.
Office Action dated Mar. 17, 2008 in U.S. Appl. No, 10/339,000.
Final Office Action mailed Oct. 9, 2008 for U.S. Appl. No. 10/339,000.
Office Action dated Apr. 2, 2007 in U.S. Appl. No. 10/339,612.
Final Office Action dated Sep. 20, 2007 in U.S. Appl. No. 10/339,612.
Office Action dated Jan. 25, 2008 in U.S. Appl. No. 10/339,612.
Final Office Action dated Aug. 6, 2008 in U.S. Appl. No. 10/339,612.
Notice of Abandonment for Failure to Respond to Office Action for U.S. Appl. No. 10/339,612 mailed Mar. 31, 2009.
Office Action dated Jun. 21, 2005, in U.S. Appl. No. 10/339,108.
Office Action Dated Sep. 16, 2005 U.S. Appl. No. 10/339,108.
Final Office Action dated Mar. 16, 2006 in U.S. Appl. No. 10/339,108.
Final Office Action dated Sep. 7, 2006 in U.S. Appl. No. 10/339,108.
Office Action Dated Mar. 5, 3007, U.S. Appl. No. 10/339,108.
Final Office Action dated Aug. 23, 2007 in U.S. Appl. No. 10/339,108.
Notice of Abandonment for Faliure to Respond to Office Action for U.S. Appl. No. 10/339,108 mailed Nov. 4, 2008.
Compounding Today, "Ciprofloxacin Suspension in Syrup NF," 2009.
Dundee et al., "Pediatric Counseling and Medication Management Services: Opportunities for Community Pharmacies," Journal of the American Pharmaceutical Association. Jul./Aug. 2002, vol. 42, No. 4.
Walgreens, "Pharmacy Manual," Jan. 2010.
Allen, Loyd; "A Spoonful from Paddock Helps the Medicine Go Down," Secundum Artem, vol. 4, No. 2; 2007.
Shrewsbury, Bob; "Theophylline—Guaifenesin Syrup." University of North Carolina, Chapel Hill. Jan. 2011.
RS Software, "CompoundAssist Manual" 2002.
FDA, "Pediatric Dispensing Considerations," 2006.
Braun, "Pinnacle TPN Management System," Dec. 2006.
Herbein, Orsolya; "FLAVORx Favorable Flavors Program," 2009.
Cram et al., "Challenges of developing palatable oral paediatric formulations," International Journal of Pharmaceutics 365; 2009.
Non-Final Office Action for U.S. Appl. No. 12/121,495 mailed Mar. 13, 2013.

(56) References Cited

OTHER PUBLICATIONS

Non-Final Office Action for U.S. Appl. No. 13/040,710 mailed Apr. 3, 2013.
Paul Brians, Common Errors in English Usage, Retrieved Nov. 21, 2007.
Non-Final Office Action for U.S. Appl. No. 12/121,495 mailed Apr. 12, 2011.
Final Office Action for U.S. Appl. No. 12/357,882 mailed Apr. 13, 2011.
Notice of Allowance for U.S. Appl. No. 10/339,000 mailed Apr. 9, 2009.
Final Office Action for U.S. Appl. No. 12/121,495 mailed Oct. 13, 2011.
Final Office Action for U.S. Appl. No. 12/571,152 mailed Mar. 20, 2012.
Final Office Action for U.S. Appl. No. 12/748,129 mailed Jun. 5, 2012.
Final Office Action for U.S. Appl. No. 12/748,129 mailed Nov. 23, 2012.
Notice of Allowance for U.S. Appl. No. 12/357,882 mailed Aug. 5, 2011.
Notice of Allowance for U.S. Appl. No. 12/748,129 mailed May 31, 2013.
Final Office Action for U.S. Appl. No. 13/040,710 mailed Aug. 9, 2013.
PK Software, "The Compounder 4, Professional Compounding and Pharmacy Management Software."
Final Office Action for U.S. Appl. No. 12/121,495 mailed Nov. 20, 2013.
Final Office Action for U.S. Appl. No. 13/040,710 mailed Nov. 20, 2013.

\* cited by examiner

US 8,688,468 B1

SYSTEMS AND METHODS FOR VERIFYING DOSAGES ASSOCIATED WITH HEALTHCARE TRANSACTIONS

FIELD OF THE INVENTION

Aspects of the invention relate generally to healthcare transactions, and more particularly, to the verification of dosages associated with healthcare transactions.

BACKGROUND OF THE INVENTION

Medication errors are increasingly recognized as an important cause of preventable deaths and injuries. A significant percentage of medication errors occur when a prescribed dosage or prescribed strength of a given drug is an incorrect or inappropriate dosage for the patient. Certain groups of patients, such as pediatric patients, are often subject to greater health risk and preventable drug-related morbidity as a result of dosage errors. These errors may be occurring due to healthcare providers, such as physicians or pharmacies, failing to adjust a dosage based on a weight, body size, and/or body surface area of the patient. Depending upon the drug prescribed, the consequences of prescribing an incorrect dosage could be dangerous, or even fatal, especially when the prescribed drug has a narrow margin of therapeutic safety or when the patient is particularly vulnerable. Another potential consequence is a lack of efficacy, such as may occur when a lower dosage is filled than what was prescribed.

Therefore, systems and methods for verifying dosages associated with healthcare transactions are desirable. Further, systems and methods for verifying dosages prescribed to infants are desirable.

BRIEF DESCRIPTION OF THE INVENTION

Some or all of the above needs and/or problems may be addressed by certain embodiments of the invention. Embodiments of the invention may include systems, methods, and apparatus for verifying dosages associated with healthcare transactions. In one embodiment, a computer-implemented method for verifying dosages associated with healthcare transactions is provided. A healthcare transaction may be received from a healthcare provider computer. The received healthcare transaction may include information associated with a patient and a prescribed product. Based at least in part on the received information, an age of the patient may be determined. Based upon the determined age, a probable weight for the patient may be determined. The probable weight may be utilized to determine whether a prescribed dosage for the product is an appropriate dosage for the patient. In certain embodiments, the above operations may be performed by one or more computers associated with a service provider.

In accordance with another embodiment of the invention, a system for verifying dosages associated with healthcare transactions may be provided. The system may include at least one memory and at least one processor. The at least one memory may be operable to store computer-executable instructions. The at least one processor may be configured to access the at least one memory and execute the computer-executable instructions to: receive, from a healthcare provider computer, a healthcare transaction comprising information associated with a patient and a prescribed product; determine, based at least in part on the received information, an age of the patient; determine, based at least in part upon the determined age, a probable weight for the patient; and determine, utilizing the probable weight, whether a prescribed dosage for the product is an appropriate dosage.

In accordance with yet another embodiment of the invention, a computer-implemented method for verifying dosages associated with healthcare transactions is provided. A healthcare transaction may be received from a healthcare provider computer. Based upon information included in the received transaction, a product associated with transaction, a prescribed dosage for the product, and an age of a patient associated with the transaction may be determined. A weight of the patient may be estimated based at least in part upon the determined age. One or more correct dosages for the product may be determined based upon the estimated weight, and the prescribed dosage may be compared to the one or more correct dosages. Based at least in part upon the comparison, a determination may be made as to whether the prescribed dosage is an appropriate dosage. In certain embodiments, the above operations may be performed by one or more computers associated with a service provider.

Additional systems, methods, apparatus, features, and aspects may be realized through the techniques of various embodiments of the invention. Other embodiments and aspects of the invention are described in detail herein with reference to the description and to the drawings and are considered a part of the claimed invention.

BRIEF DESCRIPTION OF THE DRAWINGS

Reference will now be made to the accompanying drawings, which are not necessarily drawn to scale, and wherein.

DETAILED DESCRIPTION

Figure 1:
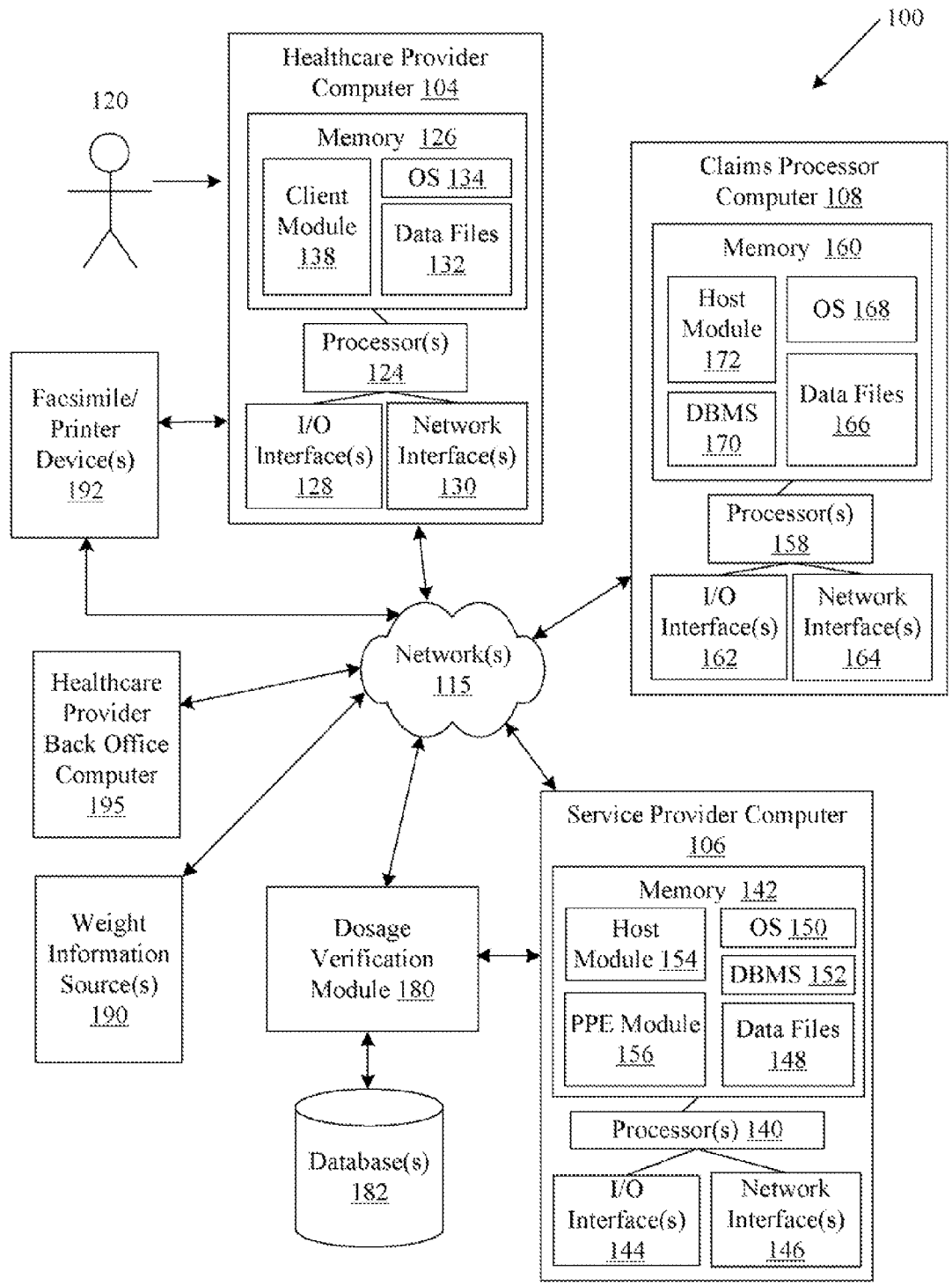
FIG. 1 illustrates an example overview of a system that facilitates the verification of dosages associated with healthcare transactions, according to an example embodiment of the invention.

Embodiments of the invention now will be described more fully hereinafter with reference to the accompanying drawings, in which embodiments of the invention are shown. This invention may, however, be embodied in many different forms and should not be construed as limited to the embodiments set forth herein, rather, these embodiments are provided so that this disclosure will be thorough and complete, and will fully convey the scope of the invention to those skilled in the art. Like numbers refer to like elements throughout.

Embodiments of the invention may include systems, methods, and apparatus for verifying dosages associated with healthcare transactions. In certain embodiments, a healthcare transaction may be received from a healthcare provider computer. A wide variety of different types of healthcare transactions may be received, such as prescription claim transactions and/or electronic prescription orders. Additionally, a wide variety of information may be included in the healthcare transaction, such as information associated with a prescribed product (e.g., a prescription drug), a prescribed dosage associated with the product, and/or information associated with a patient (e.g., a patient name, a patient date of birth, etc.). Utilizing information included in the healthcare transaction, such as a patient date of birth, an age of the patient may be identified or determined. In certain embodiments, the patient age may be compared to one or more age thresholds, and a determination may be made based upon the comparison as to whether the patient falls within a predetermined group of patients. For example, a determination may be made as to whether the patient is an infant. The determined patient age may be utilized to determine or estimate a probable weight or a range of probable weights associated with the patient. In certain embodiments, information that correlates patient ages and weights, such as a weight-for-age percentile chart or a suitable lookup table, may be accessed and utilized to determine a probable weight for the patient. Additionally, as desired in certain embodiments, a probable weight for the patient may be determined based at least in part on the patient's gender.

Once a patient's probable weight has been determined, the probable weight may be utilized in a determination as to whether the prescribed dosage for the product is an appropriate dosage. For example, an expected dosage or range of expected dosages for the patient may be determined based upon the probable weight, and the expected dosage(s) may be compared to the prescribed dosage. A wide variety of different processing techniques may be utilized as desired to determine whether a prescribed dosage is an appropriate dosage. For example, a determination may be made as to whether the prescribed dosage falls outside of a minimum and/or maximum allowable dosage for the patient. As another example, a determination may be made as to whether the prescribed dosage matches one or more typical or common dosages for the product. As yet another example, various statistical analyses may be performed in order to determine a likelihood that the prescribed dosage is an appropriate dosage.

For purposes of this disclosure, a healthcare transaction may include any suitable transaction or communication that is processed by a service provider configured to act as a router or communications hub between healthcare providers and/or claims processors. One example of a healthcare transaction is a healthcare claim transaction that is communicated from a healthcare provider, such as a pharmacy, to a service provider for routing or other communication to a claims processor for adjudication. Another example of a healthcare transaction is an electronic prescription order or request that is communicated from a first healthcare provider, such as a physician, through the service provider to a second healthcare provider, such as a pharmacy.

System Overview

An example system 100 for verifying dosages associated with healthcare transactions will now be described illustratively with respect to FIG. 1. As shown in FIG. 1, the system 100 may include any number of healthcare provider computers 104, service provider computers 106, and claims processor computers 108. As desired, each of the healthcare provider computers 104, service provider computers 106, and claims processor computers 108 may include one or more processing devices that may be configured for accessing and reading associated computer-readable media having stored thereon data and/or computer-executable instructions for implementing the various methods of the invention.

Additionally, in certain embodiments, the service provider computer 106 may include or otherwise be in communication with a dosage verification module 180 or a dosage verification application, which may access and/or be in communication with one or more suitable databases or storage devices 182. The dosage verification module 180 may receive information associated with one or more healthcare transactions and evaluate the prescribed dosages included in the healthcare transactions. For example, the dosage verification module 180 may identify or determine an age of a patient associated with a healthcare transaction. The dosage verification module 180 may then utilize the patient age to determine or estimate a probable weight and/or range of probable weights for the patient. The probable weight may then be utilized to determine or calculate one or more expected dosages and/or range of dosages for the patient. The expected dosages and/or ranges may then be utilized to evaluate the prescribed dosage in order to determine whether the prescribed dosage is appropriate. If it is determined that a prescribed dosage is not appropriate, then the dosage verification module 180 may generate one or more rejection and/or error messages associated with the healthcare transaction and direct the communication of the message(s) to a healthcare provider that submitted the healthcare transaction. In this regard, potentially dangerous or fatal dosage errors may be identified and corrected prior to dispensing or providing a product (e.g., a prescription drug) to a patient.

Generally, network devices and systems, including one or more of the healthcare provider computer 104, service provider computer 106, and claims processor computer 108 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well-known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computer 104, service provider computer 106, and claims processor computer 108 may be in communication with each other via one or more networks, such as network 115, which as described below can include one or more separate or shared private and public networks, including the Internet or a publicly switched telephone network. Each of these components—the healthcare provider computer 104, service provider computer 106, claims processor computer 108, and the network 115—will now be discussed in further detail.

Any number of healthcare provider computers 104 may be provided. Each healthcare provider computer may be associated with a healthcare provider, for example, a pharmacy, physician's office, hospital, etc. The healthcare provider computer 104 may be any suitable processor-driven device that facilitates the processing of healthcare requests (e.g., prescription orders) made by or on behalf of patients or consumers and the communication of information associated with healthcare transaction requests (e.g., healthcare claim transactions, healthcare claim requests, electronic prescription orders, etc.) to the service provider computer 106. For example, the healthcare provider computer 104 may be a computing device that includes any number of server computers, mainframe computers, networked computers, desktop computers, personal computers, digital assistants, personal digital assistants, digital tablets, Internet appliances, application-specific circuits, microcontrollers, minicomputers, and/or any other processor-based device(s). In certain embodiments, the healthcare provider computer 104 may be a suitable point of sale device associated with a healthcare provider. The execution of the computer-implemented instructions by the healthcare provider computer 104 may form a special purpose computer or other particular machine that is operable to facilitate the processing of healthcare requests (e.g., prescription orders) made by or on behalf of patients and the communication of information associated with healthcare transaction requests (e.g., claim requests and/or healthcare claim transactions, electronic prescription orders, etc.) to a service provider computer 106. Additionally, in certain embodiments of the invention, the operations and/or control of the healthcare provider computer 104 may be distributed among several processing components.

In addition to having one or more processors 124, the healthcare provider computer 104 may include one or more memory devices 126, one or more input/output ("I/O") interface(s) 128, and one or more network interface(s) 130. The memory devices 126 may be any suitable memory device, for example, caches, read only memory devices, random access memory devices, magnetic storage devices, removable storage devices, etc. The memory devices 126 may store data, executable instructions, and/or various program modules utilized by the healthcare provider computer 104, for example, data files 132, an operating system ("OS") 134, and/or a client module 138. The data files 132 may include any suitable data that facilitates the receipt and/or processing of healthcare requests (e.g., prescription orders) by the healthcare provider computer 104 and the generation and/or processing of healthcare transaction requests (e.g., healthcare claim requests, healthcare claim transactions, eligibility transaction requests, etc.) that are communicated to the service provider computer 106. For example, the data files 132 may include, but are not limited to, information associated with the service provider computer 106, information associated with one or more claims processors or payers, information associated with other healthcare provider computers, and/or information associated with one or more healthcare transaction requests. The OS 134 may be a suitable software module that controls the general operation of the healthcare provider computer 104. The OS 134 may also facilitate the execution of other software modules by the one or more processors 124, for example, the client module 138. The OS 134 may be, but is not limited to, Microsoft Windows®, Apple OSX™, Linux, Unix, or a mainframe operating system. The client module 138 may be an Internet browser or other software, including a dedicated program, for interacting with the service provider computer 106. For example, a user such as a pharmacist or other pharmacy employee, may utilize the client module 138 in preparing and providing a prescription claim request to the service provider computer 106 for delivery to one or more appropriate claims processor computers 108, for adjudication or other coverage/benefits determination. The healthcare provider computer 104 may also utilize the client module 138 to retrieve or otherwise receive data, messages, or responses from the service provider computer 106 and/or other components of the system 100. For example, in certain embodiments, the client module 138 may be utilized to receive information associated with a service provided by the dosage verification module 180.

In operation, the healthcare provider computer 104 may receive information associated with a healthcare request (e.g., prescription order) from a patient. As one example, the healthcare provider computer 104 may receive information associated with a healthcare request for a patient at a point of sale, such as in a pharmacy during a prescription fulfillment or purchase transaction or at a physician's office during the provision of a healthcare service. As another example, the healthcare provider computer 104 may electronically receive a healthcare request from a physician computer, a patient computer, or other patient device. The healthcare provider computer 104 may generate a healthcare transaction request (e.g., healthcare claim request, healthcare claim transaction, electronic prescription order, etc.), and information associated with the healthcare transaction request may be communicated to the service provider computer 106. The healthcare provider computer 104 may also utilize the client module 138 to retrieve or otherwise receive data, messages, or responses from the service provider computer 106 and/or other components of the system 100.

The one or more I/O interfaces 128 may facilitate communication between the healthcare provider computer 104 and one or more input/output devices, for example, one or more user interface devices, such as a display, keypad, control panel, touch screen display, remote control, microphone, etc., that facilitate user interaction with the healthcare provider computer 104. For example, the one or more I/O interfaces 128 may facilitate entry of information associated with a healthcare transaction request (e.g., healthcare claim transaction, healthcare claim request, eligibility transaction request, etc.) by an employee of a healthcare provider, such as a pharmacy employee. The one or more network interfaces 130 may facilitate connection of the healthcare provider computer 104 to one or more suitable networks, for example, the network 115 illustrated in FIG. 1. In this regard, the healthcare provider computer 104 may receive and/or communicate information to other network components of the system 100, such as the service provider computer 106.

In certain embodiments, the healthcare provider computer 104 can further include a facsimile/printer device 192 operative to receive and print one or more messages received from the service provider computer 106 and/or the dosage verification module 180. For example, as described further below, the service provider computer 106 may on occasion transmit a facsimile or other printing command to the healthcare provider computer 104 and/or the facsimile/printer device 192 containing one or more messages associated with dosage evaluation and/or verification. The transmission from the service provider computer 106 may be directly to the facsimile/printer device 192, such as may be accomplished via a network 115 (e.g., Internet, cellular network, wireless network, or any other similar network, etc.). In another embodiment, the transmission may be to the healthcare provider computer 104, which in turn communicates with and commands the facsimile/printer device 192 to print a message. Although the term facsimile/printer device is used throughout this description, it is appreciated that any other device operable to receive and print or generate a display of a notification message may be included within the scope of a facsimile/printer device. Examples of other devices include, but are not limited to, a mobile device (e.g., cellular telephone, personal digital assistant, personal information device, etc.), a personal computer, a computer kiosk, or any other handheld or mobile devices.

With continued reference to FIG. 1, the service provider computer 106 may include, but is not limited to, any suitable processor-driven device that is configured for receiving, processing, and fulfilling requests from the healthcare provider computer 104 and/or claims processor computer 108 relating to prescription, pharmacy, benefits, eligibility, and/or healthcare transactions and/or other activities. In certain embodiments, the service provider computer 106 may be a switch/router that routes healthcare transactions comprising requests and replies/responses. For example, the service provider computer 106 may route billing requests and/or prescription claim requests communicated from various healthcare provider computers 104 to appropriate claims processor computers, which may be associated with pharmacy benefits managers ("PBM"), insurers, government payers, or claims clearinghouses. The service provider computer 106 may then route adjudicated replies or other responses to the claim requests from the claims processor computers 108 to the healthcare provider computers 104. Likewise, the service provider computer 106 may also route electronic prescription orders communicated from a first healthcare provider computer 104 (e.g., physician computer) to another healthcare provider computer 104 (e.g., a pharmacy computer) for receipt into a pharmacy management system. In certain embodiments, the service provider computer 106 may include a suitable host server, host module, or other software that facilitates the receipt of a healthcare transaction request or reply and/or the routing of the transaction request or reply to a recipient. Any number of healthcare provider computers and/or claims processor computers may be in communication with the service provider computer 106 as desired in various embodiments of the invention.

The service provider computer 106 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 106 may be controlled by computer-executed or computer-implemented instructions that are executed by one or more processors associated with the service provider computer 106 to form a special purpose computer or other particular machine that is operable to facilitate the receipt, routing, and/or processing of healthcare transactions. The one or more processors that control the operations of the service provider computer 106 may be incorporated into the service provider computer 106 and/or may be in communication with the service provider computer 106 via one or more suitable networks. In certain embodiments of the invention, the operations and/or control of the service provider computer 106 may be distributed among several processing components.

Similar to the healthcare provider computer 104, the service provider computer 106 may include one or more processors 140, one or more memory devices 142, one or more input/output ("I/O") interface(s) 144, and one or more network interfaces 146. The one or more memory devices 142 may be any suitable memory devices, for example, caches, read only memory devices, random access memory devices, magnetic storage devices, removable memory devices, etc. The one or more memory devices 142 may store data, executable instructions, and/or various program modules utilized by the service provider computer 106, for example, data files 148, an operating system ("OS") 150, the host module 154, a pre- and post-edit ("PPE") module 156, and a database management system ("DBMS") 152 to facilitate management of the data files 148 and other data stored in the memory devices 142 and/or one or more databases or data storage devices 182. The OS 150 may be, but is not limited to, Microsoft Windows®, Apple OSX™, Linux, Unix, or a mainframe operating system. The OS 150 may be a suitable software module that controls the general operation of the service provider computer 106 and/or that facilitates the execution of other software modules.

The PPE module 156 may be operable to perform one or more pre-edits on a received healthcare transaction, such as a claim transaction or an electronic prescription order, prior to routing or otherwise communicating the received healthcare transaction to a recipient, such as a claims processor computer 108 or another healthcare provider computer. Additionally, the PPE module 156 may be operable to perform one or more post-edits on a response or reply (e.g., an adjudicated reply) that is received from a claims processor computer 108 (or other healthcare provider computer) for a healthcare transaction prior to routing the response to the healthcare provider computer 104. A wide variety of different pre-edits and/or post-edits may be performed as desired in various embodiments of the invention. In certain embodiments, the dosage verification module 180 may be a pre-edit that is selectively performed by the PPE module 156 if a dosage verification service is activated for a healthcare provider that submitted a healthcare transaction.

According to an embodiment of the invention, the data files 148 may store healthcare transaction records associated with communications received from various healthcare provider computers 104 and/or various claims processor computers 108. The data files 148 may also store any number of suitable routing tables that facilitate determining the destination of communications received from a healthcare provider computer 104 or claims processor computer 108. The host module 154 may receive, process, and respond to requests from the client module 138 of a healthcare provider computer 104, and may further receive, process, and respond to requests of the host module 172 of a claims processor computer 108. The service provider computer 106 may include additional program modules for performing other processing methods described herein. Those of ordinary skill in the art will appreciate that the service provider computer 106 may include alternate and/or additional components, hardware or software without departing from example embodiments of the invention.

A dosage verification module 180 or dosage verification application may also be operative with the service provider computer 106. The dosage verification module 180 may include computer-executable instructions for determining whether a prescribed dosage associated with a healthcare transaction is an appropriate dosage for the patient. In certain embodiments, the dosage verification module 180 may identify or determine an age of a patient associated with a healthcare transaction, and the dosage verification module 180 may utilize the age to determine or estimate a potential weight or range of potential weights for the patient. For example, the dosage verification module 180 may estimate a potential weight of an infant based upon the infant's age. The dosage verification module 180 may then utilize the determined potential weight to assess the prescribed dosage and determine whether the prescribed dosage is appropriate.

In operation, the dosage verification module 180 may receive information associated with a healthcare transaction. A wide variety of information may be included in a received healthcare transaction, such as an identifier of a product included in the healthcare transaction (e.g., a National Drug Code ("NDC"), a Universal Product Code ("UPC"), a Stock Keeping Unit ("SKU"), etc.), information associated with a patient, an identifier of a healthcare provider (e.g., a pharmacy identifier, store number, etc.), an identifier of a recipient of the transaction (e.g., a claims processor computer, another healthcare provider computer, etc.), a date of the healthcare transaction, etc.

Once information associated with a healthcare transaction has been received, the dosage verification module 180 may analyze at least a portion of the received information in order to identify a product associated with the healthcare transaction. For example, a product may be identified based upon a product name and/or a product identifier (e.g., NDC, UPC, SKU, etc.). Once a product has been identified, a determination may be made as to whether a dosage verification service is supported for the identified product. In other words, a determination may be made as to whether acceptable dosage information is available for the product. If the product is supported, the dosage verification module 180 may determine whether patient age information is included in the healthcare transaction. For example, the dosage verification module 180 may determine whether a patient age and/or date of birth that can be utilized to determine the patient age is included. If no age information is included, the dosage verification module 180 may generate a rejection message or other message for the transaction requesting appropriate age information, and the dosage verification module 180 may direct the communication of the generated message to the healthcare provider computer 104. Otherwise, if age information is identified, the dosage verification module 180 may optionally determine whether the patient's age satisfies any number of age parameters or thresholds, such as a maximum age associated with a dosage verification service. In certain embodiments, the dosage verification module 180 may utilize the age to determine whether the patient is an infant for which a dosage verification service should be provided.

According to an aspect of the invention, the dosage verification module 180 may utilize the patient age to determine or estimate a potential weight and/or a range of potential weights for the patient. A wide variety of suitable techniques may be utilized as desired to determine a weight based upon a patient age. For example, the patient age may be utilized as a reference to access information that correlates ages to potential weights and/or to ranges of potential weights. In certain embodiments, the patient age may be utilized to identify a point within an age/weight correlation chart, such as an infant or child growth chart developed by the National Center for Health Statistics (NCHS) and provided by the Centers for Disease Control and Prevention (CDC). In other embodiments, the patient age may be utilized to access a lookup table that correlates patient ages and weights. In this regard, a potential weight and/or range of potential weights may be identified for the patient. As desired, a gender of the patient and/or an identity of a product may additionally be taken into account when determining a potential weight. For example, different weight correlation information may be provided for male and female patients, and the appropriate information may be accessed utilizing the gender of the patient. As another example, different weight correlation information may be utilized for various products and/or classifications of products. As desired, potential weight information and/or age/weight correlation information may be received from any number of suitable information sources, such as the weight information sources 190 described in greater detail below. As a result of determining or estimating a potential weight of a patient, a healthcare provider is not required to manually enter patient weight data. As an alternative to determining or estimating a potential weight, the dosage verification module 180 may identify patient weight information that is included in the healthcare transaction.

Once a potential weight (or range of weights) has been determined or estimated, the dosage verification module 180 may identify, determine, and/or access appropriate dosage information for a patient having the potential weight. A wide variety of appropriate dosage information may be identified as desired in various embodiments of the invention, such as a minimum allowable dosage, a minimum number of doses per day, a maximum allowable dosage, a maximum number of doses per day, and/or one or more typical or common dosages and/or number of doses per day. The appropriate dosage information may include per day dosage information, per use or application dosage information, and/or information associated with a number of suitable daily doses for the product. The dosage information may then be compared to a prescribed dosage included in the healthcare transaction in order to determine whether the prescribed dosage is an appropriate dosage. As desired, a wide variety of different dosage verification procedures may be utilized to determine whether a dosage is appropriate, such as an absolute dosage verification procedure, a typical dosage verification procedure, and/or a likelihood dosage verification procedure. Each of these procedures is described in greater detail below with reference to FIG. 5.

If the dosage verification module 180 determines that a prescribed dosage is an appropriate dosage for the patient, then the dosage verification module 180 may mark the healthcare transaction as approved for routing or other communication by the service provider computer 106 to a recipient, such as the claims processor computer 108. If, however, the dosage verification module 180 determines that a prescribed dosage is not an appropriate dosage or is likely not an appropriate dosage, then the dosage verification module 180 may take one or more control actions. As one example, the dosage verification module 180 may generate a rejection message or other message associated with the healthcare transaction, and the dosage verification module 180 may direct the communication of the message to the healthcare provider computer 104 and/or the facsimile/printer device 192. A wide variety of information may be included in a generated message as desired in various embodiments, including but not limited to, an indication that the prescribed dosage is not appropriate, information associated with the determined potential weight, an invitation to modify the prescribed dosage and resubmit the healthcare transaction, and/or override information (e.g., an override code) that may be utilized to suppress a portion or all of the processing of the dosage verification module 180 during a resubmission of the healthcare transaction.

The data storage devices 182 or databases may be operable to store data as well as information associated with various rules and/or parameters that may be utilized by the dosage verification module 180. Examples of data that may be stored include, but are not limited to, healthcare transaction information, age/weight correlation information (e.g., growth charts, lookup tables, etc.), information associated with processed healthcare transactions, patient information, etc. In certain embodiments, rules may be received from one or more other components of the system 100, such as the healthcare provider computer 104, and/or a healthcare provider back office computer 195 that is associated with a group of healthcare providers (e.g., a pharmacy chain), and at least a portion of the received rules may be stored. A wide variety of rules and/or parameters may be received and/or stored, including but not limited to, rules associated with the generation and/or communication of messages, rules associated with the types of age/weight correlation information to utilize, rules associated with dosage verification techniques to utilize, rules associated with products and/or classifications of products (e.g., therapeutic classes) that should be evaluated, etc. In addition to or as an alternative to utilizing certain rules associated with a healthcare provider or group of healthcare providers, one or more default rules may be accessed and utilized by the dosage verification module 180. Additionally, in certain embodiments, the data storage devices 182 may be operable to store information associated with healthcare transactions, responses and/or replies, and/or processing performed by the service provider computer 106. In certain embodiments, the data storage devices 182 may additionally store billing information associated with the processing performed by the dosage verification module 180. Additionally, as desired, the data storage devices 182 may store various reports associated with the processing performed by the dosage verification module 180. The data storage devices 182 may be accessible by the dosage verification module 180 and/or the service provider computer 106.

In certain embodiments, the dosage verification module 180 and/or the service provider computer 106 may be operable to generate one or more reports that are associated with processed healthcare transactions. A wide variety of different types of reports may be generated as desired in various embodiments of the invention. Additionally, a wide variety of different information may be incorporated into generated reports, including but not limited to, healthcare transaction information, invocation information associated with the dosage verification module 180, generated error messages, identified dosage errors, information associated with healthcare providers and/or healthcare provider computers associated with identified dosage errors, and/or billing information associated with the invocation of the dosage verification module 180. Reports may be sorted or formatted utilizing a wide variety of different criteria, parameters, and/or techniques. Additionally, the dosage verification module 180 and/or the service provider computer 106 may communicate or direct the communication of generated reports to one or more other components of the system 100, for example, the healthcare provider computer 104 and/or the healthcare provider back office computer 195. A wide variety of different techniques and/or software programs may be utilized to format a generated report. For example, a report may be formatted as a comma-separated-value ("csv") file, as a spreadsheet file, as a word processor file, as a text file, etc. Additionally, a wide variety of different communication techniques may be utilized to communicate a report to the recipient, including but not limited to, email, short message service ("SMS") messaging, other electronic communications, snail mail, etc. A report may be pushed to a recipient by the dosage verification module 180 or other reporting module, or, alternatively pulled from the dosage verification module 180 by a recipient submitting a request for one or more reports. Additionally, in certain embodiments, a report may be made available for download from an appropriate web site or server, such as a web site hosted by the service provider computer 106.

Messages and/or reports (e.g., transaction reports and/or other reports) that are generated by the dosage verification module 180 and/or the service provider computer 106 may be communicated to a recipient (e.g., the healthcare provider computer 104, the healthcare provider back office computer 195, etc.) by the dosage verification module 180 in either a direct or indirect manner. In certain embodiments, messages and/or reports may be directly communicated to a recipient by the dosage verification module 180 via one or more suitable networks 115. In other embodiments, the messages and/or reports may be communicated by the dosage verification module 180 to another component of the system 100, such as the service provider computer 106, for communication to a recipient. For messages and/or reports that are communicated to a healthcare provider, the communications may be sent to the healthcare provider computer 104 and/or to another device associated with the healthcare provider, such as a facsimile/printer device 192.

Figure 3:
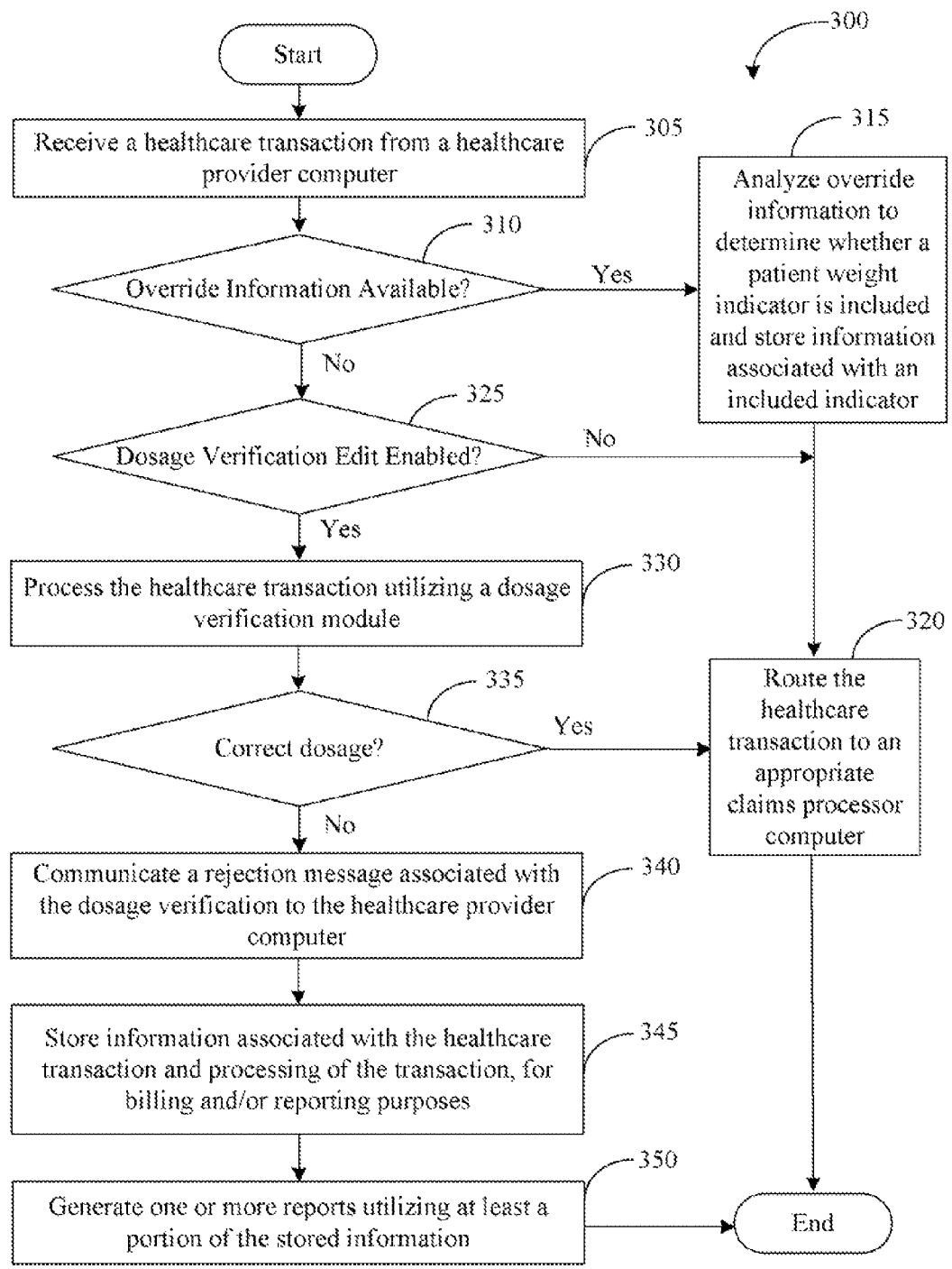
FIG. 3 is a flow diagram of an example method for processing a healthcare transaction, according to an example embodiment of the invention.

The operations of the dosage verification module 180 and/or the data storage devices 182 are described in greater detail below with reference to FIGS. 3-5.

With continued reference to the service provider computer 106, the one or more I/O interfaces 144 may facilitate communication between the service provider computer 106 and one or more input/output devices, for example, one or more user interface devices, such as a display, keypad, control panel, touch screen display, remote control, microphone, etc., that facilitate user interaction with the service provider computer 106. The one or more network interfaces 146 may facilitate connection of the service provider computer 106 to one or more suitable networks, for example, the network 115 illustrated in FIG. 1. In this regard, the service provider computer 106 may communicate with other components of the system 100.

With continued reference to FIG. 1, any number of claims processor computers 108 may be provided. Each claims processor computer 108 may be any suitable processor-driven device that facilitates receiving, processing, and/or fulfilling healthcare transactions, such as healthcare claim transactions, received from the service provider computer 106. For example, a claims processor computer 108 may be a processor-driven device associated with a pharmacy benefits manager ("PBM"), an insurer, a government payer, or a claims clearinghouse. As desired, the claims processor computer 108 may include any number of special purpose computers or other particular machines, application-specific circuits, microcontrollers, personal computers, minicomputers, mainframe computers, servers, and the like. In certain embodiments, the operations of a claims processor computer 108 may be controlled by computer-executed or computer-implemented instructions that are executed by one or more processors associated with the claims processor computer 108 to form a special purpose computer or other particular machine that is operable to facilitate the receipt, processing, and/or fulfillment of healthcare transaction requests received from the service provider computer 106. The one or more processors that control the operations of the claims processor computer 108 may be incorporated into the claims processor computer 108 and/or in communication with the claims processor computer 108 via one or more suitable networks. In certain embodiments of the invention, the operations and/or control of the claims processor computer 108 may be distributed among several processing components.

Similar to other components of the system 100, each claims processor computer 108 may include one or more processors 158, one or more memory devices 160, one or more input/output ("I/O") interface(s) 162, and one or more network interfaces 164. The one or more memory devices 160 may be any suitable memory devices, for example, caches, read only memory devices, random access memory devices, magnetic storage devices, removable memory devices, etc. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process and/or audit healthcare transactions, for example, patient profiles, patient insurance information, other information associated with a patient, information associated with a healthcare provider, information associated with financial coverage information, etc. The OS 168 may be a suitable software module that controls the general operation of the claims processor computer 108. The OS 168 may also facilitate the execution of other software modules by the one or more processors 158, for example, the DBMS 170 and/or the host module 172. The OS 168 may be, but is not limited to, Microsoft Windows®, Apple OSX™, Linux, Unix, or a mainframe operating system. The DBMS 170 may be a suitable software module that facilitates access and management of one or more databases that are utilized to store information that is utilized by the claims processor computer 108 in various embodiments of the invention. The host module 172 may initiate, receive, process, and/or respond to healthcare transaction requests, such as healthcare claim transactions or claim requests, from the host module 154 of the service provider computer 106. The claims processor computer 108 may include additional program modules for performing other pre-processing or post-processing methods described herein, such as an audit process. Those of ordinary skill in the art will appreciate that the claims processor computer 108 may include alternate and/or additional components, hardware or software without departing from example embodiments of the invention.

The one or more I/O interfaces 162 may facilitate communication between the claims processor computer 108 and one or more input/output devices, for example, one or more user interface devices, such as a display, keypad, control panel, touch screen display, remote control, microphone, etc., that facilitate user interaction with the claims processor computer 108. The one or more network interfaces 164 may facilitate connection of the claims processor computer 108 to one or more suitable networks, for example, the network 115 illustrated in FIG. 1. In this regard, the claims processor computer 108 may receive healthcare transactions and/or other communications from the service provider computer 106, and the claims processor computer 108 may communicate information associated with processing transactions to the service provider.

With continued reference to FIG. 1, any number of weight information sources 190 may be utilized as desired in various embodiments of the invention. A weight information source 190 may include one or more processor-driven devices or computers that are configured to communicate or provide age/weight correlation information, such as growth charts and/or information associated with lookup tables, to the service provider computer 106 and/or the dosage verification module 180. As desired in certain embodiments, information may be communicated by the weight information source 190 upon request and/or at designated (e.g., periodic) points in time, such as once a week, once a month, and/or based upon an alteration or update of the information. In certain embodiments, a weight information source 190 may include components that are similar to those of other devices included in the system 100, such as the healthcare provider computer 104.

The healthcare provider back office computer 195 may be one or more computers associated with a group of healthcare providers, such as a chain of pharmacies. The healthcare provider back office computer 195 may include components that are similar to those of other devices included in the system 100, such as the healthcare provider computer 104. For example, the healthcare provider back office computer 195 may be a processor-driven device that is operable or configured to provide, to the service provider computer 106 and/or the dosage verification module 180, any number of parameters, rules, and/or preferences associated with the provision of a dosage verification service. Additionally, the healthcare provider back office computer 195 may be operable or configured to receive various reports and/or billing information associated with the services provided by the dosage verification module 180.

The network 115 may include any telecommunication and/or data network, whether public, private, or a combination thereof, including a local area network, a wide area network, an intranet, the Internet, intermediate handheld data transfer devices, and/or any combination thereof and may be wired and/or wireless. The network 115 may also allow for real time, offline, and/or batch transactions to be transmitted between or among the healthcare provider computers 104*a-n*, the service provider computer 106, and the claims processor computers 108*a-n*. Due to network connectivity, various methodologies as described herein may be practiced in the context of distributed computing environments. Although the service provider computer 106 is shown for simplicity as being in communication with the healthcare provider computer 104, the claims processor computer 108, and/or the dosage verification module 180 via one intervening network 115, it is to be understood that any other network configuration is possible. For example, network 115 may include a plurality of networks, each with devices such as gateways and routers for providing connectivity between or among networks 115. Instead of or in addition to a network 115, dedicated communication links may be used to connect the various devices in accordance with an example embodiment of the invention. For example, the service provider computer 106 may form the basis of network 115 that interconnects the healthcare provider computer 104 and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the service provider computer 106 (or other computer) may be implemented as a specialized processing machine that includes hardware and/or software for performing the methods described herein. In addition, at least a portion of the processor and/or processing capabilities of the service provider computer 106 and/or the dosage verification module 180, may be implemented as part of a claims processor computer 108. Accordingly, embodiments of the invention should not be construed as being limited to any particular operating environment, system architecture, or device configuration.

Operational Overview

Figure 2A:
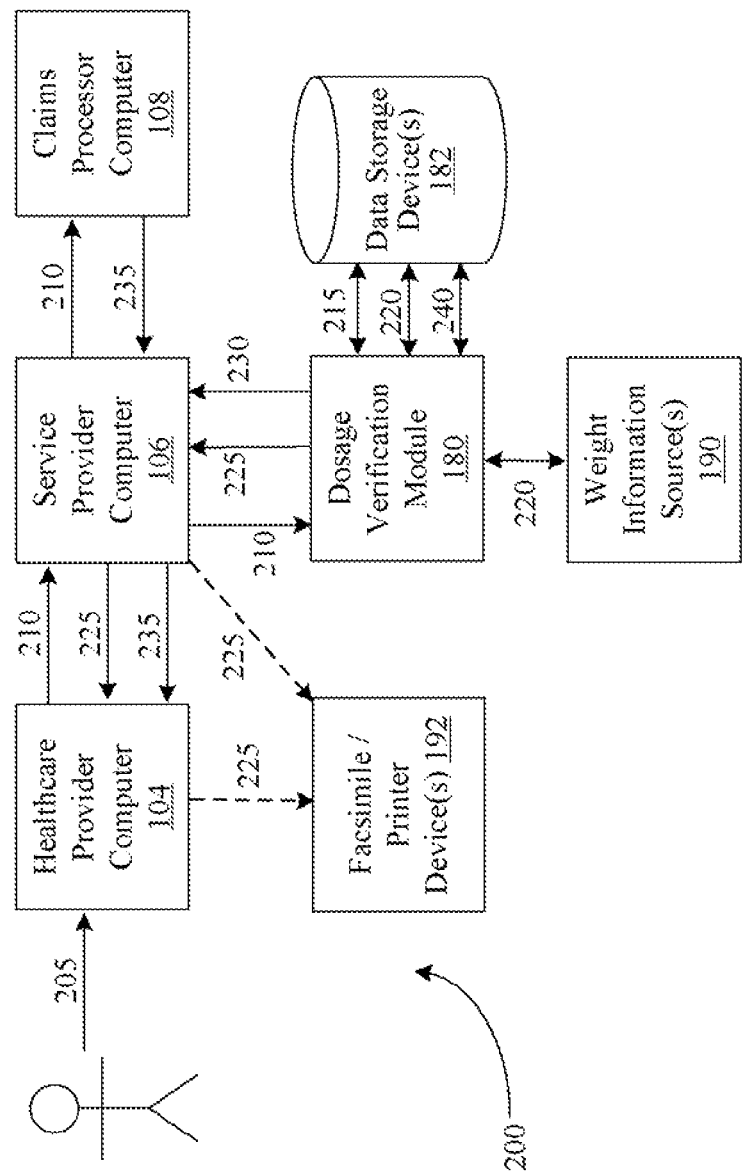
FIGS. 2A and 2B are diagrams of example data flows for verifying dosages of healthcare transactions as they are communicated through a service provider, according to an example embodiment of the invention.

FIG. 2A is a diagram of an example data flow 200 for verifying dosages of healthcare transactions as they are communicated through a service provider, such as the service provider computer 106 illustrated in FIG. 1. With reference to FIG. 2A, a healthcare provider computer, such as the healthcare provider computer 104 illustrated in FIG. 1, may receive a healthcare request 205 from a patient. The healthcare request 205 may be a prescription order that is received in-person or electronically as desired in various embodiments of the invention. For example, a patient may seek to fill a prescription for one or more drugs, medications, and/or other products at a pharmacy location or store. As another example, a patient may communicate a healthcare request 205, such as a request to till a prescription, to a healthcare provider computer 104 via one or more suitable network connections. For example, a purchase request may be communicated to a healthcare provider computer 104 from a customer computer via a web portal hosted by the healthcare provider computer 104. In addition, a physician/clinic/hospital computer can also communicate a healthcare request 205 as an electronic prescription order (e.g., an E-SCRIPT) to the healthcare provider computer 104.

The healthcare provider computer 104 may receive and process the request 205 to generate a healthcare transaction request 210, which may be in the form of a prescription claim request. The generated healthcare transaction request 210 may be communicated by the healthcare provider computer 104 to the service provider computer 106. Accordingly, the healthcare transaction request 210 may be received by the service provider computer 106. According to an example embodiment of the invention, the healthcare transaction request 210 may be in accordance with a version of a National Council for Prescription Drug Programs ("NCPDP") Telecommunication Standard, although other standards may be utilized as well. As desired, the healthcare transaction request 210 may include a Banking Identification Number ("BIN") and/or Processor Control Number ("PCN") for identifying a claims processor computer, such the claims processor computer 108 illustrated in FIG. 1, as a destination of the healthcare transaction request 210. In addition, the healthcare transaction request 210 may also include information relating to the patient, payer, prescriber, healthcare provider, and/or the prescribed drug or product. As an example, the healthcare transaction request 210 received by the service provider computer 106 may include one or more of the following information:

- Payer ID/Routing Information for each identified payer or potential payer
    - Banking Identification Number (BIN) and Processor Control Number (PCN) that designates an intended destination of the healthcare transaction request 210
- Patient Information
    - Name (e.g., Patient Last Name, Patient First Name, etc.)
    - Date of Birth of Patient
    - Age of Patient
    - Gender
    - Weight
    - Patient Address (e.g., Street Address, Zip Code, etc.)
    - Patient Contact Information (e.g., Patient Telephone Number)
    - Patient ID or other identifier
- Insurance/Coverage Information
    - Cardholder Name (e.g., Cardholder First Name, Cardholder Last Name)
    - Cardholder ID and/or other identifier (e.g., person code)
- Provider (e.g., Prescriber, Pharmacy) Information
    - Prescriber Information
        - Primary Care Provider ID or other identifier (e.g., National Provider Identifier (NPI) code)
        - Primary Care Provider Name (e.g., Last Name, First Name)
        - Prescriber ID or other identifier (e.g., NPI code, DEA number)
        - Prescriber Name (e.g., Last Name, First Name)
        - Prescriber Contact Information (e.g., Telephone Number)
    - Pharmacy or other Healthcare Provider Information (e.g., store name, chain identifier, etc.)
    - Pharmacy or other Healthcare Provider ID (e.g., NPI code)
- Claim Information
    - Drug or product information (e.g., National Drug Code (NDC))
    - Prescription/Service Reference Number
    - Date Prescription Written
    - Quantity Dispensed
    - Number of Days Supply
    - Diagnosis/Condition
    - Pricing information for the drug or product (e.g., network price, Usual & Customary price)
    - Date of Service.

The service provider computer 106 may receive the healthcare transaction request 210 from the healthcare provider computer 104, and the service provider computer 106 may process the healthcare transaction request 210. As desired, the service provider computer 106 may perform one or more pre-edits on the healthcare transaction request 210. The pre-edits may verify, add, and/or edit information included in the healthcare transaction request 210 prior to the healthcare transaction request 210 being communicated to the claims processor computer 108. If no rejections are triggered or generated by any pre-edits performed for the transaction 210, then the healthcare transaction request 210 and/or a copy thereof may be routed or otherwise communicated by the service provider computer 106 to the claims processor computer 108 for adjudication. According to an example embodiment, the service provider computer 106 may utilize at least a portion of the information included in the healthcare transaction request 210, such as a BIN/PCN, to determine the appropriate claims processor computer 108 to route the healthcare transaction request 210 to. The service provider computer 106 may also include a routing table, perhaps stored in memory, for determining which claims processor computer 108 to route the healthcare transaction request 210 to.

According to an aspect of the invention, a determination may be made as to whether a dosage verification service should be performed for the healthcare transaction request 210 prior to communicating the request 210 to the claims processor computer 108. For example, a determination may be made as to whether a dosage verification service or edit has been activated or enabled for a healthcare provider that submitted the healthcare transaction request 210. If it is determined that a dosage verification service is enabled, then the healthcare transaction request 210, a copy thereof, and/or information included in the request 210 may be communicated to the dosage verification module 180.

In certain embodiments, the dosage verification module 180 may access or otherwise obtain one or more rules 215, parameters, and/or other information associated with performing a dosage verification service. For example, rules 215 may be accessed from one or more suitable data storage devices 182. A wide variety of rules may be accessed as desired in various embodiments of the invention, including but not limited to, rules associated with products for which a dosage verification service is supported, rules associated with products specified by the healthcare provider or a group of healthcare providers for which a dosage verification service should be provided, patient eligibility parameters and/or thresholds (e.g., age thresholds, etc.), rules associated with verification techniques to be utilized, dosage parameters for an identified product, billing rules, reporting rules, etc.

The dosage verification module 180 may identify or determine an age of a patient associated with the healthcare transaction request 210. For example, an age may be determined based upon a patient date of birth included in the request 210. As desired, the dosage verification module 180 may determine whether the patient age satisfies one or more age thresholds. For example, a determination may be made as to whether the patient is an infant. If the dosage verification module 180 determines that age parameters are not satisfied, then an approval 230 to communicate the healthcare transaction request 210 to the claims processor computer 108 may be communicated to the service provider computer 106. Otherwise, the determined age may be utilized to determine a potential weight or range of potential weights for the patient. In certain embodiments, weight information 220 may be accessed or obtained from any number of suitable sources, for example, the data storage devices 182 and/or one or more weight information sources, such as the weight information sources 190 illustrated in FIG. 1. A wide variety of weight information 220 may be accessed as desired in various embodiments. For example, information that correlates patient age and potential weight(s) may be accessed. In certain embodiments, growth charts and/or age/weight lookup tables may be accessed. As desired, the access of age/weight correlation information may be based upon a gender of the patient and/or the product associated with the healthcare transaction request 210. For example, different correlation information may be accessed for male patients and female patients. As another example, different correlation information may be accessed for different products or classifications of products (e.g., therapeutic classifications). As an alternative to determining a potential weight or range of weights based upon patient age, the dosage verification module 180 may identify patient weight information that is included in the healthcare transaction request 210 or stored for the patient in the data storage devices 182.

Once a potential weight or range of weights is identified or determined for the patient, the dosage verification module 180 may utilize the potential weight(s) to determine one or more acceptable dosages for the product. In certain embodiments, the product may be identified based upon information included in the healthcare transaction request 210, such as a product name, NDC, UPC, or SKU, and acceptable dosage information may be identified and accessed for the identified product. A wide variety of acceptable dosage information may be accessed, such as a maximum dosage and/or number of doses per day, a minimum dosage and/or number of doses per day, one or more typical or common dosages and/or doses per day, and/or various rules associated with evaluating a prescribed dosage. A prescribed dosage included in the healthcare transaction may then be evaluated utilizing the acceptable dosage information. As desired, a daily prescribed dosage may be determined prior to the evaluation. Additionally, as desired, a number of prescribed doses per day may be determined prior to the evaluation. Based upon an evaluation, a determination may be made as to whether the prescribed dosage is an acceptable dosage for the patient. A wide variety of dosage evaluation techniques may be utilized as desired in various embodiments of the invention, for example, absolute dosage evaluation techniques, typical dosage evaluation techniques, and/or likelihood dosage evaluation techniques.

If the dosage verification module 180 determines that the prescribed dosage is not an acceptable dosage, then the dosage verification module 180 may generate one or more messages 225 associated with the determination. For example, a rejection message 225 for the healthcare transaction request 210 may be generated. The generated message 225 may include a wide variety of different information as desired in various embodiments, such as an indication that the prescribed dosage was determined to be an unacceptable dosage for the patient, an indication of an acceptable dosage or range of dosages, an invitation to alter the prescribed dosage and resubmit the healthcare transaction request 210, and/or override information that may be utilized to suppress a portion or all of the operations of the dosage verification module 180 during a resubmission of the healthcare transaction request 210. Once generated, the dosage verification module 180 may direct the communication of the message 225 to the healthcare provider computer 104 and/or to the facsimile/printer devices 192. In certain embodiments, the message 225 may be communicated directly to a healthcare provider by the dosage verification module 180. In other embodiments, the message 225 may be communicated through the service provider computer 106.

If, however, the dosage verification module 180 determines that the prescribed dosage is an acceptable dosage, then the dosage verification module 180 may communicate a message 230 or other information to the service provider computer 106 indicating that the healthcare transaction request 210 may be communicated to the claims processor computer 108. The healthcare transaction request 210 and/or a copy thereof may be routed or otherwise communicated by the service provider computer 106 to the claims processor computer 108 for adjudication. According to an example embodiment, the service provider computer 106 may utilize at least a portion of the information included in the healthcare transaction request 210, such as a BIN/PCN, to determine the appropriate claims processor computer 108 to route the healthcare transaction request 210 to. The service provider computer 106 may also include a routing table, perhaps stored in memory, for determining which claims processor computer 108 to route the healthcare transaction request 210 to.

The claims processor computer 108 may receive and adjudicate or otherwise process the healthcare transaction request 210. For example, the claims processor computer 108 may determine benefits coverage for the healthcare transaction request 210 according to an adjudication process associated with eligibility, pricing, and/or utilization review. The claims processor computer 108 may transmit a response 235, such as an adjudicated reply for the healthcare transaction request 210, to the service provider computer 106. The service provider computer 106 may receive the response 235 from the claims processor computer 108. As desired, the service provider computer 106 may perform any number of post-edits on the response 235. The service provider computer 106 may then route or otherwise communicate the response 235 or a copy thereof to the healthcare provider computer 104.

As desired in certain embodiments, the dosage verification module 180 may be configured to store a wide variety of information 240 associated with the processing of the healthcare transaction request 210. Examples of suitable information that may be stored include, but are not limited to, information included in the healthcare transaction request 210, age information for a patient, weight indications for a patient, potential weight and/or weight range information for the patient, acceptable dosage information, an indication of a rejection, information associated with the processing of the transaction request 210, information associated with the invocation of the dosage verification module 180, etc. In certain embodiments, as described above with reference to FIG. 1, the dosage verification module 180 and/or the service provider computer 106 may be configured to generate a wide variety of reports associated with the processing of healthcare transactions. Generated reports may then be communicated to one or more recipients, such as the healthcare provider computer 104 and/or a healthcare provider back office computer 195. A wide variety of suitable communications techniques, for example, electronic mail, short message service ("SMS") messaging, other electronic communications, snail mail, etc., may be utilized as desired to communicate generated reports to one or more recipients.

Additionally, in certain embodiments, information associated with the invocation of the dosage verification module 180 may be communicated to an appropriate billing system associated with the service provider computer 106 in order to facilitate billing customers, such as healthcare providers, for the services provided by the dosage verification module 180. Alternatively, the dosage verification module 180 may alter a billing code or other field of the healthcare transaction request 210 and/or response 235 to a value indicating that the transaction or request has been evaluated or processed by the dosage verification module 180. The altered billing code may be recognized during subsequent or further processing of the healthcare transaction request 210 or response 235, such as further processing by the service provider computer 106, in order to facilitate billing.

Although FIG. 2A illustrates the processing of a healthcare transaction request, a healthcare request associated with an electronic prescription order may also be received and processed by the service provider computer 106 in a similar manner. For example, a healthcare provider computer associated with a physician's office may receive a healthcare request (e.g., a prescription order) from a patient, such as a healthcare request for a prescription drug or product. The healthcare provider computer may utilize the received healthcare request to generate an electronic prescription order. The generated electronic prescription order may be communicated by the healthcare provider computer to the service provider computer 106. The electronic prescription order may then be processed by the dosage verification module 180 in a similar manner as that described above for a healthcare transaction request 210.

Figure 2B:
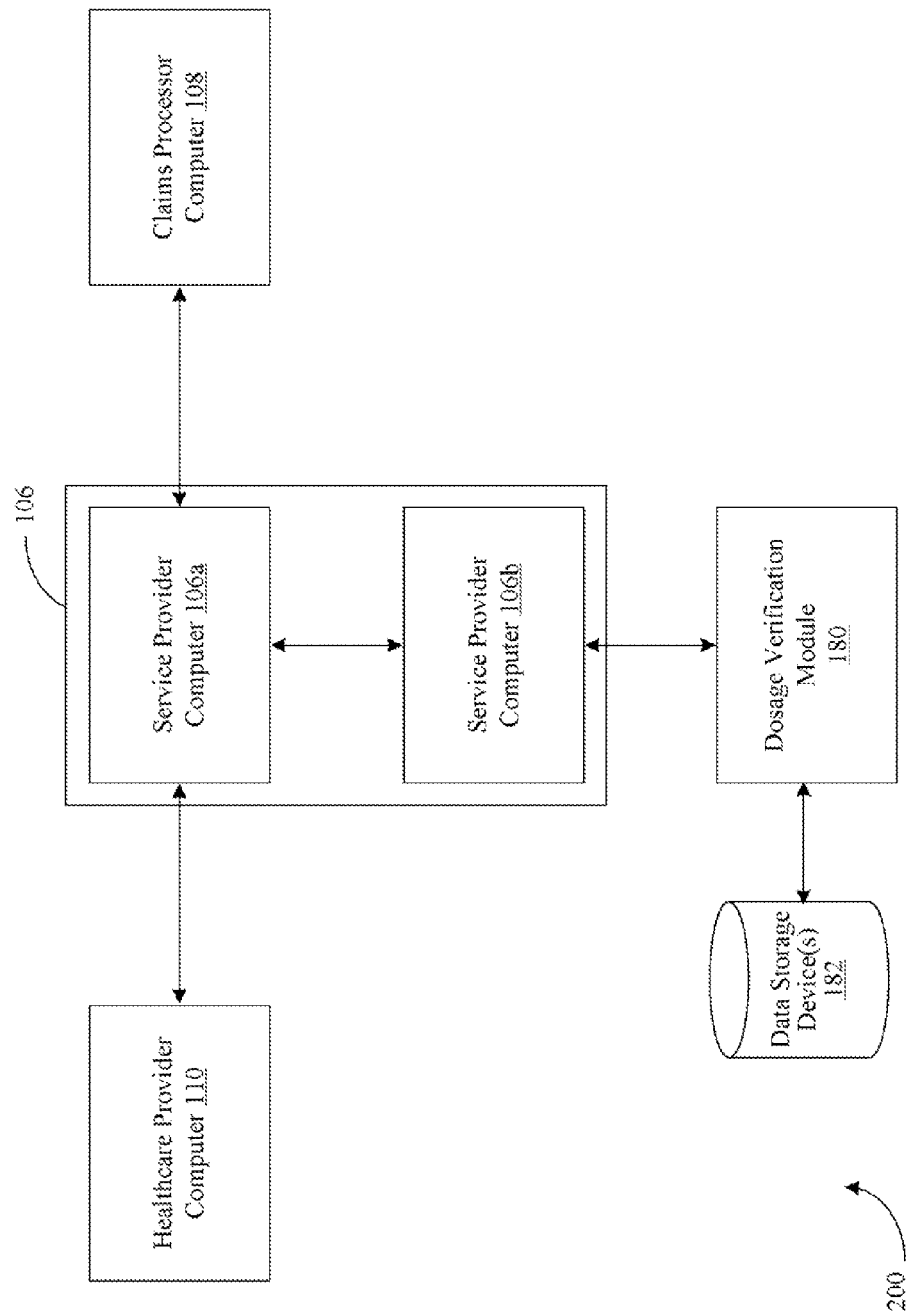

It will be appreciated that variations of the data flow 200 illustrated in FIG. 2A may be utilized in accordance with various embodiments of the invention. For example, as shown in FIG. 2B, the service provider computer 106 may be comprised of two or more distinct service provider computers 106a and 106b that are in communication with each other. Service provider computer 106a may be operative with one or more healthcare provider computers and/or claims processor computers, such as the healthcare provider computer 104 and claims processor computer 108 illustrated in FIG. 1. However, service provider computer 106b may have a data processing arrangement with service provider computer 106a. Under the data processing agreement, the service provider computer 106a may be permitted to utilize or offer services of the service provider computer 106b, including those of the dosage verification module 180. For example, a first service provider may communicate healthcare transaction information and/or other information to a second service provider for processing and/or the performance of a dosage verification service.

As described herein, healthcare transactions may be examined as they are routed to or through a service provider computer 106. In this regard, a dosage verification service may be provided in real time or near real time as the healthcare transactions are routed to or through the service provider computer 106. FIG. 3 is a flow diagram of an example method 300 for processing a healthcare transaction, according to an example embodiment of the invention. The method 300 may be performed by a suitable service provider computer and/or an associated dosage verification module, such as the service provider computer 106 and the dosage verification module 180 illustrated in FIG. 1. The method 300 may begin at block 305.

At block 305, a healthcare transaction or healthcare transaction request, such as a healthcare claim transaction or an electronic prescription order, may be received from a healthcare provider computer, such as the healthcare provider computer 104 illustrated in FIG. 1. A wide variety of information may be included in the received healthcare transaction, such as product information, prescribed dosage information, information associated with a patient, and/or information identifying a claims processor computer to which the healthcare transaction should be communicated, such as the claims processor computer 108 illustrated in FIG. 1.

At block 310, a determination may be made as to whether override information is included in the healthcare transaction or otherwise available for the transaction. A wide variety of override information may be associated with the transaction, such as an override code. Override information may be utilized to suppress one or more edits that are performed on the healthcare transaction. For example, override information may be utilized to suppress a portion or all of the processing that is performed by the dosage verification module 180. If it is determined at block 310 that override information is available, then operations may continue at block 315.

At block 315, which may be optional in certain embodiments of the invention, the override information and/or other information included in the transaction may be analyzed to determine whether a patient weight indicator is included. For example, a patient weight indicator indicating that the patient has a weight that is greater than or less than a normal weight range may be identified. In this regard, situations in which a patient falls outside of a normal weight distribution or normal weight range (e.g., severely overweight and/or underweight infants) may be identified. If a patient weight indicator is identified, the patient weight indicator may be stored in association with other information for the patient. Additionally, as desired, the patient weight indicator, other stored patient weight indicators for the patient, and/or information associated with a number of times that a weight indicator has been received for the patient may be utilized to determine a potential weight for the patient. In certain embodiments, prescribed dosage information for the patient may also be utilized to determine a potential weight. For example, if one or more weight indicators are received for a particular patient indicating that the patient is an overweight infant, then a potential weight for the patient may be determined based upon the weight indicators and/or prescribed dosage amounts for the patient. The determined potential weight may be utilized in a dosage verification service for the patient. As desired, the determined potential weight may be stored for access during the process of subsequently received healthcare transactions.

At block 320, the healthcare transaction may be routed or otherwise communicated to the claims processor computer 108 or to another recipient, such as another healthcare provider computer. For example, the healthcare transaction may be routed to the claims processor computer for adjudication.

If, however, it is determined at block 310 that override information is not available, then operations may continue at block 325. At block 325, one or more pre-edits and/or evaluations may be performed on the received healthcare transaction as desired in various embodiments of the invention. For example, one or more pre-edits may be performed by a suitable PPE module, such as the PPE module 156 illustrated in FIG. 1. Additionally, a determination may be made at block 325 as to whether a dosage verification edit has been enabled or activated for processing the healthcare transaction. For example, rules or preferences associated with processing healthcare transactions (e.g., rules received from the healthcare provider computer 104 and/or a healthcare provider back office computer 195) may be analyzed in order to determine whether an eligibility edit is enabled. In other words, a determination may be made as to whether dosage verification has been enabled for a healthcare provider that submitted the healthcare transaction or for a group of healthcare providers (e.g., a pharmacy chain) to which the healthcare provider belongs. If it is determined at block 325 that a dosage verification edit has not been enabled, then operations may continue at block 320 described above. If, however, it is determined at block 325 that a dosage verification edit has been enabled, then operations may continue at block 330.

At block 330, the healthcare transaction may be processed by a suitable dosage verification module 180 or dosage verification application. The dosage verification module 180 may, for example, determine a probable weight or range of probable weights for the patient and determine, based at least in part upon the probable weight(s), whether a prescribed dosage is an appropriate dosage for the patient. One example of the operations that may be performed by the dosage verification module 180 in order to process a healthcare transaction is described in greater detail below with reference to FIGS. 4A and 4B.

At block 335, a determination may be made as to whether the dosage verification module 180 identified the prescribed dosage as a correct dosage or an appropriate dosage. If it is determined at block 335 that the dosage is a correct or appropriate dosage, then operations may continue at block 320 described above, and the healthcare transaction reply may be routed or otherwise communicated to the claims processor computer 108. If, however, it is determined at block 335 that the prescribed dosage is not a correct or appropriate dosage, then operations may continue at block 340. At block 340, a message, such as a rejection message for the healthcare transaction, may be communicated to the healthcare provider computer 104 and/or to a suitable facsimile/printer device, such as the facsimile/printer device 192 illustrated in FIG. 1. A wide variety of information may be included in the communicated message as desired in various embodiments of the invention, including but not limited to, an indication that the prescribed dosage was identified as an incorrect or inappropriate dosage, information associated with a correct or appropriate dosage and/or range of dosages, information associated with a determined probable weight and/or range of weights for the patient, an invitation to correct the prescribed dosage and resubmit the healthcare transaction, and/or override information that may be utilized to suppress the processing of the dosage verification module 180. Although FIG. 3 describes the communication of a message when it is determined that a prescribed dosage is not an appropriate dosage, in certain embodiments of the invention, one or more messages may be communicated to the healthcare provider even when the prescribed dosage is identified as an appropriate dosage. For example, a healthcare provider preference may specify that a message associated with the dosage verification should be communicated even if the prescribed dosage is appropriate. As desired, various healthcare provider message preferences may be scoped to certain products and/or classifications of products.

At block 345, which may be optional in certain embodiments of the invention, information associated with the healthcare transaction, processing of the transaction, and/or the invocation of the dosage verification module 180 may be stored and/or communicated for billing and/or reporting purposes. As desired in certain embodiments, billing information may be communicated to a suitable billing system associated with the service provider. In other embodiments, billing information may be stored for subsequent access by a billing system or for subsequent access by another component of the service provider for communication to the billing system. Billing information may be utilized by the billing system in order to charge customers of the service provider for the service provided by the dosage verification module 180. A wide variety of different types of billing information may be stored and/or communicated as desired in various embodiments of the invention, for example, an identifier associated with the invocation of the dosage verification module 180 or a billing code (e.g., a unique billing code) associated with the invocation of the dosage verification module 180. As an alternative to storing or communicating billing information, the dosage verification module 180 may set a billing code for a healthcare transaction and/or response to the transaction to a unique billing code associated with the provided dosage verification service. The unique billing code may be identified or recognized during subsequent processing of the healthcare transaction and/or response by either the billing system or another component of the service provider computer 106. The identified billing code may then be utilized by the billing system in the generation of bills for customers of the service provider.

At block 350, which may be optional in certain embodiments of the invention, one or more reports may be generated utilizing at least a portion of the stored information. Reports may be generated by the dosage verification module 180, the service provider computer 106, and/or a separate reporting module. A wide variety of different information may be included in a generated report, including but not limited to, information extracted from one or more healthcare transactions, information associated with the processing of one or more transactions, invocation rate information for the dosage verification module 180, financial information, billing information, etc. Additionally, generated reports may be formatted and/or sorted utilizing a wide variety of different parameters and/or criteria, such as identifiers for healthcare provider computers, identifiers for healthcare providers, identifiers for products and/or services associated with healthcare claim transactions, dates of service, etc. As desired, generated reports may be communicated to one or more recipients, such as the healthcare provider computer 104 and/or the healthcare provider back office computer 195.

The method 300 may end following either block 320 or 350.

Figure 4A:
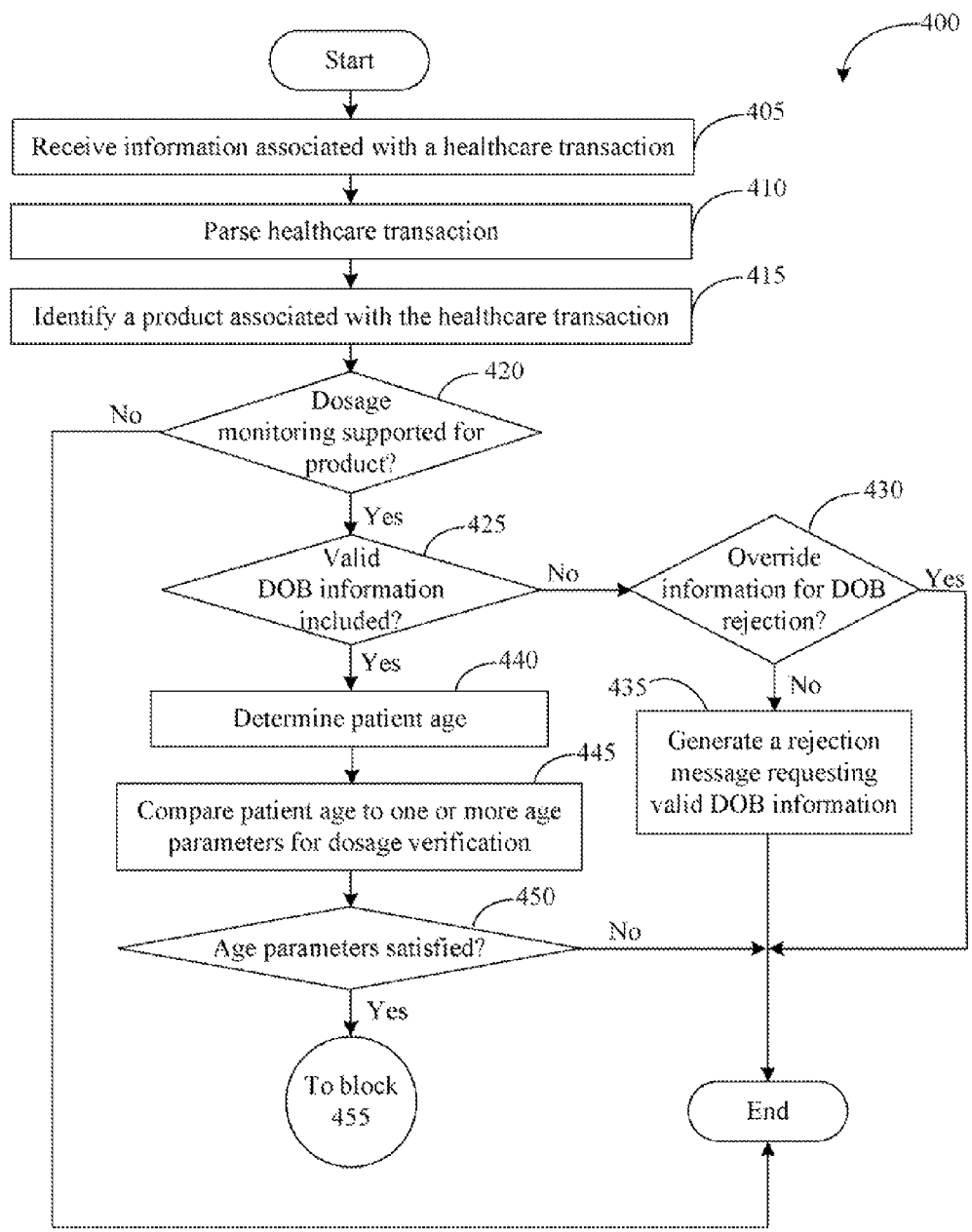
FIGS. 4A and 4B are flow diagrams of an example method for performing a dosage verification service for a healthcare transaction, according to an example embodiment of the invention.
Figure 4B:
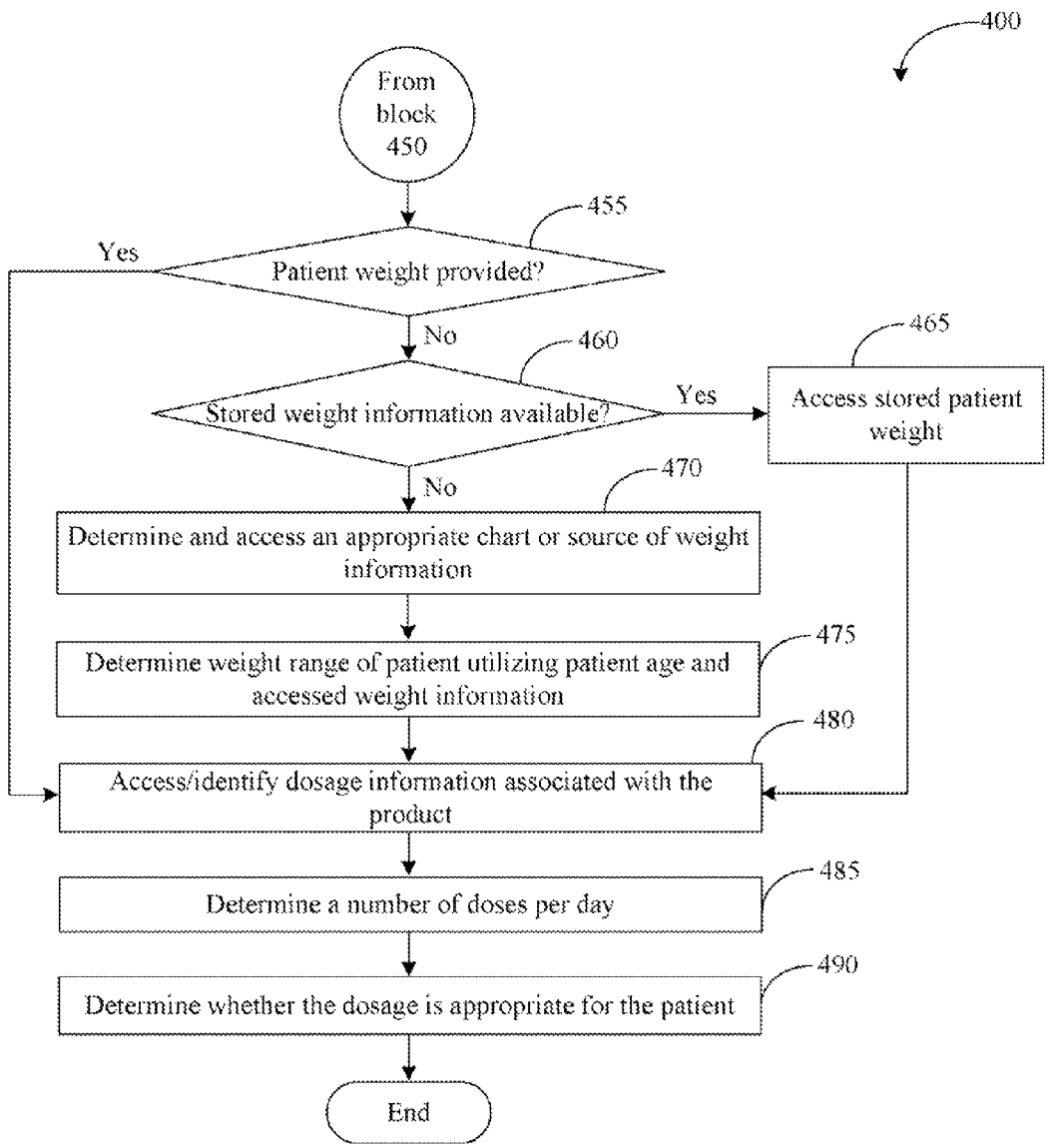

FIGS. 4A and 4B are flow diagrams of an example method 400 for performing a dosage verification service for a healthcare transaction, according to an example embodiment of the invention. The method 400 illustrated in FIG. 4 may be an example implementation of block 330 shown in FIG. 3. As such, the method 400 may be performed by a suitable service provider computer and/or dosage verification module, such as the service provider computer 106 and/or dosage verification module 180 illustrated in FIG. 1. The method 400 may begin at block 405.

At block 405, information associated with a healthcare transaction may be received. A wide variety of information associated with a healthcare transaction may be received, such as an identifier of a prescribed product, prescribed dosage information for the product, information associated with a patient, etc. As desired, the received information may be parsed at block 410.

At block 415, a product associated with the healthcare transaction may be identified. In certain embodiments, the product may be identified based upon information included in the transaction, such as a product name and/or a product identifier (e.g., a NDC; UPC, SKU, etc.). At block 420, a determination may be made as to whether dosage verification or dosage monitoring is supported for the product. For example, an identifier of the product may be compared to one or more stored identifiers associated with products for which dosage monitoring is supported, and the determination may be made based at least in part upon the comparison. Additionally, as desired, a determination may be made as to whether the healthcare provider (or a group of healthcare providers) has identified the product as a product for which dosage verification should be supported or as a product for which dosage verification should not be provided. For example, one or more preferences and/or parameters associated with the healthcare provider may be analyzed in order to determine whether the healthcare provider has opted in or opted out of a dosage verification for the identified product and/or a classification associated with the identified product. If it is determined at block 420, that dosage verification is not supported for the product, then operations may end. However, if it is determined at block 420 that dosage verification is supported for the product, then operations may continue at block 425.

At block 425, a determination may be made as to whether valid date of birth ("DOB") information is included in the healthcare transaction and/or is otherwise available for the patient. For example, the parsed information associated with the healthcare transaction may be analyzed to determine whether DOB information is included. As another example, any number of suitable memory devices, such as the databases 182 illustrated in FIG. 1, may be searched for information associated with the patient, and a determination may be made as to whether stored DOB information for the patient is identified. If it is determined at block 425 that valid DOB information is not available for the patient, then operations may continue at block 430.

At block 430, a determination may be made as to whether override information for a DOB rejection is available for the healthcare transaction. In certain embodiments, a determination may be made as to whether a previous rejection for missing or incomplete DOB information has been overridden by the healthcare provider. For example, a DOB rejection may be overridden if the healthcare provider has submitted indication an indication that the patient DOB is unknown or unavailable. A wide variety of override information may be utilized as desired in various embodiments of the invention, such as an override code and/or an indication that information is unknown or unavailable. If it is determined at block 430 that override information for a DOB rejection is available, then operations may end. Otherwise, if it is determined at block 430 that override information for a DOB rejection is not available, then operations may continue at block 435. At block 435, a message may be generated indicating that DOB information has not been provided and requesting the provision of valid DOB information. As desired, the generated message may be communicated to the healthcare provider computer 104 and/or the Facsimile/printer devices 192. In certain embodiments, the generated message may be communicated to the healthcare provider computer 104 as part of a rejection message associated with the healthcare transaction.

If, however, it is determined at block 425 that valid DOB information is available for the patient, then operations may continue at block 440. At block 440, a patient age may be determined based upon DOB information. For example, an elapsed time between the patient DOB and a current date may be calculated, and the patient age may be determined utilizing the calculated elapsed time. As desired, the determined age may be an age in years, months, and/or days. In certain embodiments, such as embodiments directed to infant patients, the determined age may represent a patient's age in months. As an alternative to determining a patient age based upon a patient DOB, patient age information included in the transaction may be identified and/or accessed from the databases 182.

At block 445, the patient age may be compared to one or more age parameters and/or thresholds associated with providing a dosage verification service. In this regard, a dosage verification service may be selectively provided based upon the age of a patient. In one example embodiment, a dosage verification service may be provided for infant patients having an age between approximately half (0.5) a month old and approximately one (1) year old. Other age thresholds and/or age ranges may be utilized as desired. In certain embodiments, utilized age parameters may be parameters that are specified by the healthcare provider or a group of providers to which the healthcare provider belongs. For example, age parameters may be parameters received from the healthcare provider computer 104 or the healthcare provider back office computer 195. In other embodiments, default parameters may be utilized. At block 450, a determination may be made as to whether the age parameters are satisfied. In other words, a determination may be made as to whether the patient age falls within a range of ages for which a dosage verification service will be provided. If it is determined at block 450 that the age parameters are not satisfied, then operations may end. If, however, it is determined at block 450 that the age parameters are satisfied, then operations may continue at block 455.

At block 455, a determination may be made as to whether a patent weight is included in the healthcare transaction or otherwise provided by the healthcare provider. If it is determined at block 455 that a patient weight or patient weight information has been provided, then operations may continue at block 480 described in greater detail below. If, however, it is determined at block 455 that patient weight information has not been provided, then operations may continue at block 460. At block 460, a determination may be made as to whether stored weight information is available for the patient. For example, a determination may be made as to whether a stored actual weight, potential weight, or potential range of weights for the patient is available. In certain embodiments, a determination may be made as to whether a stored potential weight for the patient that has been determined utilizing one or more received weight indicators is available. If it is determined at block 460 that stored weight information for the patient is available, then operations may continue at block 465, and the stored patient weight information may be accessed from memory. Operations may then continue at block 480 described in greater detail below. If, however, it is determined at block 460 that stored weight information for the patient is not available, then operations may continue at block 470.

At block 470, an appropriate source of weight information, such as age/weight correlation information, may be identified and accessed. A wide variety of different types of weight information may be accessed as desired in various embodiments of the invention, for example, growth charts, information associated with growth charts, age/weight correlation lookup tables, various formulas for calculating weight based upon patient age, etc. As desired, the identification of weight information to be accessed may be based upon any number of factors and/or parameters, such as the gender of the patient, the product associated with the healthcare transaction, a classification for the product, preferences of a healthcare provider (or group of healthcare providers), and/or preferences of a claims processor. For example, distinct growth chart(s) (or other weight information) may respectively be available for male patients and female patients, and the access of a growth chart may be based upon a gender of the patient. As another example, growth charts (or other weight information) may be available that provide different ranges of potential weights based upon age. For example, a first growth chart that provides weight ranges for the fifth percentile to the ninety-fifth percentile of patients, a second growth chart that provides weight ranges for the third percentile to the ninety-seventh percentile, and/or other growth charts may be available. An appropriate growth chart may be selected based upon one or more parameters, such as an identification of a prescribed product. For example, a growth chart that provides a relatively narrow range of potential weights may be selected for product(s) having a greater health risk associated with incorrect dosage.

At block 475, a potential weight and/or range of potential weights for the patient may be determined based at least in part upon the patient age and the accessed weight information. For example, a growth chart or lookup table that includes age/weight correlation information may be accessed utilizing the patient age in order to determine a potential weight (e.g., median weight for a given age, mean weight for a given age, etc.) and/or range of potential weights for the patient. For embodiments in which a range of potential weights is determined, any number of parameters and/or preferences may be utilized as desired to determine the range. For example, a range of weights falling between designated percentile points may be identified based upon a prescribed product, classification of the prescribed product, and/or preferences associated with a healthcare provider, group of healthcare providers, and/or claims processor. The identification of an appropriate range based upon one or more parameters may be similar to that described above for identifying weight information to be utilized. For example, a relatively narrow range of weights (e.g., weights falling between a twentieth percentile and an eightieth percentile, etc.) may be identified from a growth chart for a product having a greater health risk associated with incorrect dosage.

At block 480, dosage information associated with the prescribed product may be accessed and/or otherwise obtained. The accessed dosage information may include any suitable information associated with appropriate or correct dosages for the prescribed product. As desired, the dosage information may be accessed based upon a weight, probable weight, and/or range of probable weights associated with the patient. The accessed dosage information may include a wide variety of dosage information, such as information associated with appropriate daily dosages of the prescribed product. Additionally, a prescribed dosage for the product may be identified from the healthcare transaction. As desired, a number of prescribed doses per day for the product may also be determined at block 485. The number of prescribed doses per day may be utilized for various dosage verifications and/or to normalize a provided prescribed dosage (e.g., an instruction to take a certain amount of a product a certain number of times a day) to a daily dosage. In this regard, a comparison of the prescribed dosage to accessed daily appropriate dosage information may be facilitated.

At block 490, a determination may be made as to whether the prescribed dosage is an appropriate or correct dosage for the patient. A wide variety of different processing techniques may be utilized as desired to determine whether a prescribed dosage is an appropriate or correct dosage. For example, a determination may be made as to whether the prescribed dosage falls outside of a minimum and/or maximum allowable dosage for the patient. As another example, a determination may be made as to whether the prescribed dosage matches one or more typical or common dosages for the product. As yet another example, various statistical analyses may be performed in order to determine a likelihood that the prescribed dosage is an appropriate dosage. One example of the operations that may be utilized to determine whether a dosage is an appropriate or correct dosage is described in greater detail below with reference to FIG. 5.

The method 400 may end following either block 420, 430, 435, 450, or 490.

Figure 5:
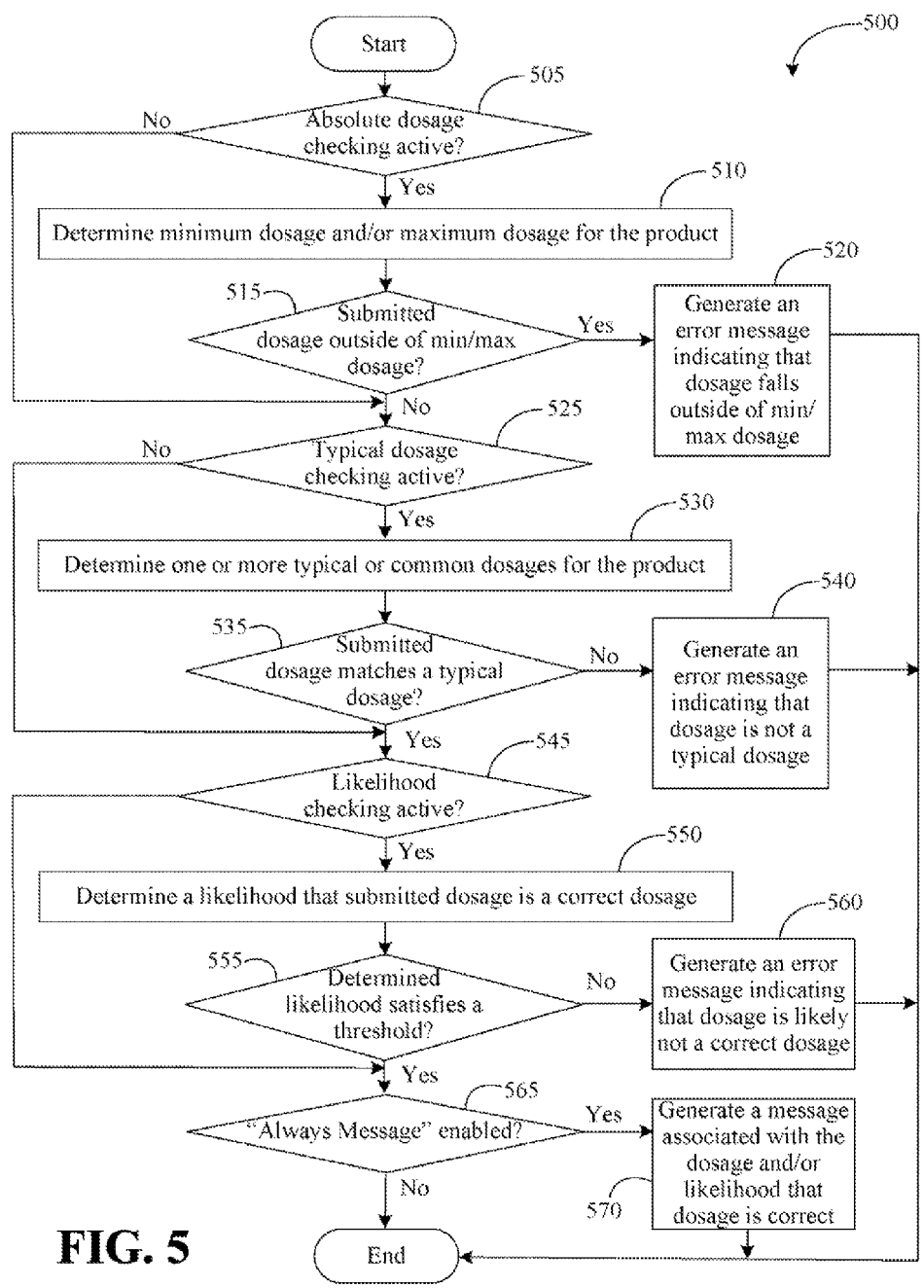
FIG. 5 is a flow diagram of an example method for verifying a dosage associated with a healthcare transaction, according to an example embodiment of the invention.

FIG. 5 is a flow diagram of an example method 500 for verifying a dosage associated with a healthcare transaction, according to an example embodiment of the invention. The method 500 illustrated in FIG. 5 may be an example implementation of block 490 shown in FIG. 4B. As such, the method 500 may be performed by a suitable service provider computer and/or dosage verification module, such as the service provider computer 106 and/or dosage verification module 180 illustrated in FIG. 1. The method 500 may begin at block 505.

For purposes of describing the verification of dosages, a dosage amount and/or a number of doses per day may be referred to as a dosage. Accordingly, the determination of whether a dosage is an appropriate or correct dosage may include a determination of whether a prescribed dosage (e.g., a prescribed daily dosage, a prescribed dosage per use, etc.) is an appropriate dosage and/or a determination of whether a prescribed number of doses per day is an appropriate or correct number of doses per day.

At block 505, a determination may be made as to whether absolute dosage checking or screening is active or enabled. For example, one or more parameters associated with the verification of dosages, such as parameters associated with the product and/or the healthcare provider, may be analyzed in order to determine whether absolute dosage checking is enabled. If it is determined at block 505 that absolute dosage checking is not active, then operations may continue at block 525 described in greater detail below. If, however, it is determined at block 505 that absolute dosage checking is active, then operations may continue at block 510.

At block 510, an absolute minimum daily dosage and/or an absolute maximum daily dosage for the product may be accessed, identified, or otherwise determined. As desired, absolute minimum and maximum daily dosages may be defined by various text references known in the healthcare industry, such as the Physicians Desk Reference ("PDR"), the United States Pharmacopedia Drug Information ("USPDI") and the like, as well as by the United States Food and Drug Administration ("USFDA"). Additionally, as desired, the absolute dosages may be identified or determined based upon a potential weight, and/or range of potential weights for the patient.

At block 515, a determination may be made as to whether the prescribed or submitted dosage falls outside of, or fails to satisfy, the absolute minimum and/or maximum dosages. If it is determined at block 515 that the prescribed or submitted dosage fails to satisfy an absolute minimum or an absolute maximum dosage for the product, then operations may continue at block 520. At block 520, an error message or other message indicating that the prescribed dosage falls outside of a minimum or maximum allowable dosage may be generated for communication to the healthcare provider computer 104 and/or the facsimile/printer devices 192. In certain embodiments, the generated message may be communicated as part of a rejection message for the healthcare transaction. Following block 520, operations may either end or additional dosage verification checks may be performed.

If, however, it is determined at block 515 that the prescribed or submitted dosage satisfies an absolute minimum and/or an absolute maximum dosage for the product, then operations may continue at block 525. At block 525, a determination may be made as to whether typical dosage checking or screening is active or enabled. For example, one or more parameters associated with the verification of dosages, such as parameters associated with the product and/or the healthcare provider, may be analyzed in order to determine whether typical or common dosage checking is enabled. If it is determined at block 525 that typical dosage checking is not active, then operations may continue at block 545 described in greater detail below. If, however, it is determined at block 525 that typical dosage checking is active, then operations may continue at block 530.

At block 530, one or more typical or common dosages for the product may be accessed, identified, or otherwise determined. For example, a common daily dosage ("CDD") and/or a most common daily dosage ("MCDD") may be identified or determined. As desired, MCDD values and CDD values may be determined by consulting a lookup table or other suitable data structure containing such information. Additionally, as desired, the typical dosages may be identified or determined based upon a potential weight, and/or range of potential weights for the patient.

At block 535, a determination may be made as to whether the prescribed or submitted dosage matches at least one typical dosage for the product. If it is determined at block 535 that the prescribed or submitted dosage does not match a typical dosage, then operations may continue at block 540. At block 540, an error message or other message indicating that the prescribed dosage is not a typical or common dosage for the prescribed product may be generated for communication to the healthcare provider computer 104 and/or the facsimile/printer devices 192. In certain embodiments, the generated message may be communicated as part of a rejection message for the healthcare transaction. Following block 540, operations may either end or additional dosage verification checks may be performed.

If however, it is determined at block 535 that the prescribed or submitted dosage matches a typical dosage, then operations may continue at block 545. At block 545, a determination may be made as to whether likelihood dosage checking or screening is active or enabled. For example, one or more parameters associated with the verification of dosages, such as parameters associated with the product and/or the healthcare provider, may be analyzed in order to determine whether likelihood dosage checking is enabled. If it is determined at block 545 that likelihood dosage checking is not active, then operations may continue at block 565 described in greater detail below. If, however, it is determined at block 545 that likelihood dosage checking is active, then operations may continue at block 550.

At block 550, a likelihood that the prescribed submitted dosage is an appropriate or correct dosage may be determined or calculated. A wide variety of suitable techniques and/or methods may be utilized to determine a likelihood that the prescribed dosage is a correct dosage. In certain embodiments, likelihood indicators for the product may be utilized to analyze the prescribed dosage. Additionally, as desired, a likelihood that the prescribed product was confused with another product may be determined as part of a dosage likelihood determination.

At block 555, a determination may be made as to whether the determined likelihood for the product satisfies at least one threshold parameter or value. For example, a determination may be made as to whether the prescribed dosage is likely an incorrect or inappropriate dosage. If, it is determined at block 555 that the prescribed dosage fails to satisfy a threshold, then operations may continue at block 560. At block 560, an error message or other message indicating that the prescribed dosage is likely an inappropriate or incorrect dosage for the prescribed product may be generated for communication to the healthcare provider computer 104 and/or the facsimile/printer devices 192. In certain embodiments, the generated message may be communicated as part of a rejection message for the healthcare transaction. Following block 560, operations may end.

If, however, it is determined at block 555 that the prescribed dosage satisfies a threshold, then operations may continue at block 565. At block 565, a determination may be made as to whether an "always message" feature is enabled or activated. For example, one or more parameters associated with dosage verification, such as parameters associated with the product and/or the healthcare provider, may be analyzed in order to determine whether a healthcare provider has specified that a message associated with dosage verification should always be communicated to the healthcare provider. As desired, the determination of whether a message should be communicated may be based upon an identity of the prescribed product. For example, a healthcare provider may specify that messages should always be generated for a relatively dangerous or risky product. As another example, a healthcare provider may specify that messages should not be received for particular products. If it is determined at block 565 that an "always message" feature is not active, then operations may end. If, however, it is determined at block 565 that an "always message" feature is active or enabled, then operations may continue at block 570. At block 570, a message associated with the dosage verification checks that have been performed and/or the likelihood that the prescribed dosage is a proper or correct dosage may be generated for communication to the healthcare provider computer 104 and/or the facsimile/printer devices 192.

The method 500 may end following either block 520, 540, 560, 565, or 570.

The operations described and shown in the methods 300, 400, 500 of FIGS. 3, 4A, 4B, and 5, respectively, may be carried out or performed in any suitable order as desired in various embodiments of the invention. Additionally, in certain embodiments, at least a portion of the operations may be carried out in parallel. Furthermore, in certain embodiments, less than or more than the operations described in FIGS. 3, 4A, 4B, and 5 may be performed.

Figure 6:
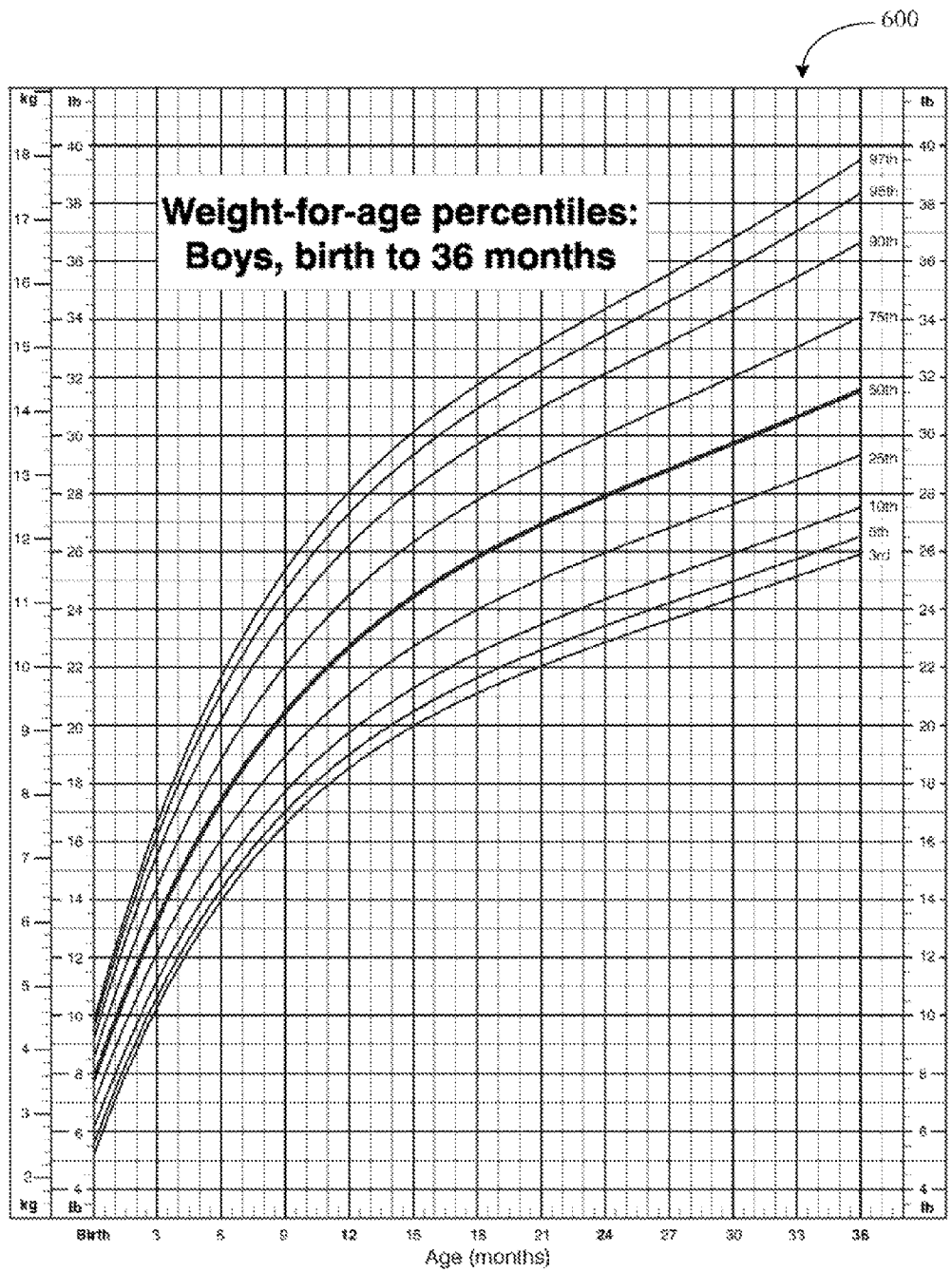
FIG. 6 is an example chart of correlation information associated with various ages and weights of patients.

FIG. 6 is an example chart 600 of correlation information associated with various ages and weights of patients. The chart 600 of FIG. 6 illustrates an example growth chart for a male patient from the time of birth until the patient is approximately three (3) years or thirty-six (36) months old. The chart 600 illustrates a range of probable weights for the patient as a function of age. At a given age, various weights for the patient are provided. Each provided weight corresponds to a percentage or percentile of individuals having the provided weight. For example, the chart 600 illustrated various percentiles ranging from the third percentile to the ninety-seventh percentile. As desired in various embodiments of the invention, information such as that illustrated in the chart 600 of FIG. 6 may be utilized to determine or calculate a potential weight and/or a potential range of weights for a patient based upon the patient's age.

Example embodiments of the invention can provide the technical effects of creating a system, method, and apparatus that determines whether a prescribed dosage for a product is an appropriate or correct dosage. Additionally, example embodiments of the invention can provide the technical effect of determining a potential weight or range of potential weights for a patient based upon a patient age. A determined potential weight may then be utilized in a determination of whether a prescribed dosage is appropriate. In this regard, incorrect dosage errors may be identified prior to a product being provided or dispensed to a patient, thereby reducing medication errors and/or drug-related morbidity. For example, infant dosage errors may be reduced.

Various block and/or flow diagrams of systems, methods, apparatuses, and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method, comprising:
receiving, from a healthcare provider computer, a healthcare transaction comprising information associated with a patient and a prescribed product;
identifying the prescribed product in the received healthcare transaction;
determining, based at least in part on the received information associated with the patient, an age of the patient;
determining, based at least in part upon the determined patient age, a patient weight;
determining whether dosage verification information is available for the identified prescribed product;
accessing, based upon the determined patient weight, dosage verification information associated with the prescribed product;
comparing the accessed dosage verification information with a prescribed dosage included in the received healthcare transaction; and
determining, based upon the comparison, whether the prescribed dosage corresponds to the dosage verification information,
wherein the above operations are performed by one or more computers associated with a service provider.

2. The method of claim 1, further comprising:
determining, based upon the determined patient age, that the patient is an infant.

3. The method of claim 1, further comprising:
accessing correlation information for patient ages and associated patient weights,
wherein determining a patient weight for the patient comprises determining the patient weight based at least in part on the accessed correlation information.

4. The method of claim 1, wherein determining a patient weight further comprises determining the patient weight based upon a gender of the patient.

5. The method of claim 1, wherein determining a patient weight comprises determining a range of weights for the patient based upon the determined age.

6. The method of claim 1, wherein determining whether a prescribed dosage for the product corresponds to the dosage verification information comprises at least one of (i) determining whether the prescribed dosage exceeds a maximum dosage for the product, (ii) determining whether the prescribed dosage is below a minimum dosage for the product, or (iii) determining that the prescribed dosage is a correct dosage.

7. The method of claim 1, wherein determining whether a prescribed dosage corresponds to the dosage verification information comprises determining that the prescribed dosage does not correspond to the dosage verification information, and further comprising:
communicating, to the healthcare provider computer, a message indicating that the prescribed dosage does not correspond to the dosage verification information.

8. The method of claim 7, further comprising:
receiving, from the healthcare provider computer subsequent to communicating the message, a weight indicator associated with the patient;
determining, based at least in part upon the received weight indicator, the patient weight; and
storing the determined patient weight for use in processing a subsequent healthcare transaction associated with the patient.

9. A system, comprising:
at least one memory operable to store computer-executable instructions; and at least one processor configured to access the at least one memory and execute the computer-executable instructions to:
- receive, from a healthcare provider computer, a healthcare transaction comprising information associated with a patient and a prescribed product;
- identify the prescribed product in the received healthcare transaction;
- determine, based at least in part on the received information, an age of the patient;
- determine, based at least in part upon the determined patient age, a patient weight;
- determine whether dosage verification information is available for the identified prescribed product;
- access, based upon the determined patient weight, dosage verification information associated with the prescribed product;
- compare the accessed dosage verification information with a prescribed dosage included in the received healthcare transaction; and
- determine, based upon the comparison, whether the prescribed dosage corresponds to the dosage verification information.

10. The system of claim 9, wherein the at least one processor is further configured to execute the computer-executable instructions to:
- determine, based upon the determined patient age, that the patient is an infant.

11. The system of claim 9, wherein the at least one processor is further configured to execute the computer-executable instructions to:
- access correlation information for patient ages and associated patient weights,
- wherein the patient weight is determined based at least in part on the accessed correlation information.

12. The system of claim 9, wherein the determined patient weight is further based upon a gender of the patient.

13. The system of claim 9, wherein the determined patient weight comprises a range of weights for the patient.

14. The system of claim 9, wherein determination of whether a prescribed dosage for the product corresponds to the dosage verification information comprises at least one of (i) a determination of whether the prescribed dosage exceeds a maximum dosage for the product, (ii) a determination of whether the prescribed dosage is below a minimum dosage for the product, or (iii) a determination that the prescribed dosage is a correct dosage.

15. The system of claim 9, wherein it is determined that the prescribed dosage does not correspond to the dosage verification information, and wherein the at least one processor is further configured to execute the computer-executable instructions to:
- direct the communication, to the healthcare provider computer, of a message indicating that the prescribed dosage does not correspond to the dosage verification information.

16. The system of claim 15, wherein the at least one processor is further configured to execute the computer-executable instructions to:
- receive, from the healthcare provider computer subsequent to communicating the message, a weight indicator associated with the patient;
- determine, based at least in part upon the received weight indicator, the patient weight; and
- store the determined patient weight for use in processing a subsequent healthcare transaction associated with the patient.

17. A computer-implemented method, comprising:
- receiving a healthcare transaction from a healthcare provider computer;
- determining, based upon information included in the received transaction, a product associated with transaction, a prescribed dosage for the product, and an age of a patient associated with the transaction;
- estimating a weight of the patient based at least in part upon the determined age;
- determining one or more dosages associated with dosage verification information for the product based upon the estimated weight;
- comparing the prescribed dosage to the one or more dosages associated with dosage verification information; and
- determining, based at least in part upon the comparison, whether the prescribed dosage corresponds to the dosage verification information,
- wherein the above operations are performed by one or more computers associated with a service provider.

18. The method of claim 17, wherein estimating a weight of the patient comprises:
- accessing correlation information for patient ages and associated weights; and
- identifying, based upon the accessed information, a weight of the patient that corresponds to the age.

* * * * *